(12) United States Patent
Miller et al.

(10) Patent No.: US 11,118,219 B2
(45) Date of Patent: *Sep. 14, 2021

(54) ISOTHERMAL AMPLIFICATION COMPONENTS AND PROCESSES

(71) Applicant: NAT DIAGNOSTICS, INC., San Diego, CA (US)

(72) Inventors: Andrew P. Miller, San Diego, CA (US); Honghua Zhang, San Diego, CA (US)

(73) Assignee: Nat Diagnostics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,958

(22) Filed: May 13, 2020

(65) Prior Publication Data

US 2020/0332340 A1 Oct. 22, 2020

Related U.S. Application Data

(63) Continuation of application No. 16/089,063, filed as application No. PCT/US2017/020921 on Mar. 6, 2017, which is a continuation-in-part of application No. 15/090,405, filed on Apr. 4, 2016, now Pat. No. 9,617,587.

(51) Int. Cl.
| | |
|---|---|
| C12Q 1/68 | (2018.01) |
| G01N 21/64 | (2006.01) |
| C12Q 1/686 | (2018.01) |
| C12Q 1/689 | (2018.01) |
| C12Q 1/6816 | (2018.01) |

(52) U.S. Cl.
CPC ............ *C12Q 1/686* (2013.01); *C12Q 1/689* (2013.01); *C12Q 1/6816* (2013.01); *G01N 21/6428* (2013.01); *C12Q 2521/101* (2013.01); *C12Q 2521/107* (2013.01); *C12Q 2527/101* (2013.01); *C12Q 2527/113* (2013.01); *C12Q 2531/113* (2013.01); *C12Q 2561/113* (2013.01); *C12Q 2600/16* (2013.01); *G01N 2021/6432* (2013.01)

(58) Field of Classification Search
CPC .................. C12Q 1/686; C12Q 1/6816; C12Q 2521/101; C12Q 2521/107; C12Q 2527/101; C12Q 2531/113; C12Q 2561/113; C12Q 2600/16; C12Q 1/6844; C12Q 2531/101; C12Q 2565/1015; G01N 21/6428; G01N 2021/6432
See application file for complete search history.

(56) References Cited

U.S. PATENT DOCUMENTS

| | | |
|---|---|---|
| 5,705,345 A | 1/1998 | Lundin et al. |
| 5,766,890 A | 6/1998 | Kacian et al. |
| 5,846,701 A | 12/1998 | Kacian et al. |
| 5,871,975 A | 2/1999 | Kacian et al. |
| 7,112,423 B2 | 9/2006 | Van Ness et al. |
| 8,268,605 B2 | 9/2012 | Sorge et al. |
| 8,338,094 B2 | 12/2012 | Gong et al. |
| 8,435,741 B2 | 5/2013 | Miyoshi et al. |
| 8,551,697 B1 | 10/2013 | Bashkirov et al. |
| 8,921,043 B2 | 12/2014 | Gardner |
| 9,562,263 B2 | 2/2017 | Maples et al. |
| 9,562,264 B2 | 2/2017 | Maples et al. |
| 9,617,586 B2 | 4/2017 | Maples et al. |
| 9,617,587 B1 | 4/2017 | Miller et al. |
| 9,689,031 B2 | 6/2017 | Maples et al. |
| 9,896,723 B2 | 2/2018 | Hicke et al. |
| 10,017,811 B2 | 7/2018 | Leamon et al. |
| 2005/0059000 A1 | 3/2005 | Sagawa et al. |
| 2005/0089918 A1 | 4/2005 | Horton |
| 2006/0154286 A1 | 7/2006 | Kong et al. |
| 2008/0182312 A1 | 7/2008 | Pack et al. |
| 2009/0017453 A1 | 1/2009 | Maples et al. |
| 2009/0155856 A1 | 6/2009 | Miyoshi et al. |
| 2009/0162856 A1 | 6/2009 | Miyoshi et al. |
| 2009/0170096 A1 | 7/2009 | Miyoshi et al. |
| 2010/0055742 A1 | 3/2010 | Nakashima et al. |
| 2010/0184154 A1 | 7/2010 | Miyoshi et al. |
| 2012/0244599 A1 | 9/2012 | Teng et al. |
| 2013/0244286 A1 | 9/2013 | Rashtchian et al. |
| 2013/0330777 A1 | 12/2013 | Zhang et al. |
| 2014/0093883 A1 | 4/2014 | Maples et al. |
| 2014/0322761 A1 | 10/2014 | Nakamura et al. |
| 2015/0064698 A1 | 3/2015 | Matsuno |
| 2016/0177289 A1 | 6/2016 | Martinez et al. |
| 2017/0137874 A1 | 5/2017 | Heller et al. |
| 2017/0183714 A1 | 6/2017 | Shen et al. |
| 2017/0240881 A1 | 8/2017 | Tatnell et al. |
| 2017/0260566 A1 | 9/2017 | Lamerton et al. |
| 2018/0023118 A1 | 1/2018 | Maples et al. |

(Continued)

FOREIGN PATENT DOCUMENTS

| | | |
|---|---|---|
| EP | 2181196 | 8/2013 |
| EP | 2657350 | 10/2013 |

(Continued)

OTHER PUBLICATIONS

Beaucage and Caruthers, "Deoxynucleoside phosphoramidites—A new class of key intermediates for deoxypolynucleotide synthesis," Tetrahedron Letters 1981, 22(20), 1859-1862.

(Continued)

*Primary Examiner* — David C Thomas

(74) *Attorney, Agent, or Firm* — Sheppard, Mullin, Richter & Hampton LLP

(57) ABSTRACT

The technology relates in part to methods and compositions for isothermal amplification of nucleic acids.

24 Claims, 6 Drawing Sheets

Specification includes a Sequence Listing.

(56) References Cited

U.S. PATENT DOCUMENTS

| | | |
|---|---|---|
| 2018/0023130 A1 | 1/2018 | Maples et al. |
| 2018/0216171 A1 | 8/2018 | Xue et al. |

FOREIGN PATENT DOCUMENTS

| | | |
|---|---|---|
| EP | 2660333 | 11/2013 |
| WO | WO2002072772 | 9/2002 |
| WO | WO2003072805 | 9/2003 |
| WO | WO2005118853 | 12/2005 |
| WO | WO2007096702 | 8/2007 |
| WO | WO2008035205 | 3/2008 |
| WO | WO2008119081 | 10/2008 |
| WO | WO2009012246 | 1/2009 |
| WO | WO2010135310 | 11/2010 |
| WO | WO2010141940 | 12/2010 |
| WO | WO2011038197 | 3/2011 |
| WO | WO2012020015 | 2/2012 |
| WO | WO2012138989 | 10/2012 |
| WO | WO2013185081 | 12/2013 |
| WO | WO2014003583 | 1/2014 |
| WO | WO2014076286 | 5/2014 |
| WO | WO2016106129 | 6/2016 |
| WO | WO2017074688 | 5/2017 |
| WO | WO2017075586 | 5/2017 |
| WO | WO2017152122 | 9/2017 |
| WO | WO2017214561 | 12/2017 |
| WO | WO2018140953 | 8/2018 |

OTHER PUBLICATIONS

Chang et al., "A thermally baffled device for highly stabilized convective PCR," Biotechnol J. 2012, 7(5), 662-666.
Corstjens et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection," Clinical Chemistry 2001, 47(10), 1885-1893.
Crain and McCloskey et al., "Applications of mass spectrometry to the characterization of oligonucleotides and nucleic acids," Current Opinion in Biotechnology 1998, 9(1), 25-34.
Examination Report dated Feb. 11, 2020 in European Patent Application No. 17711527.6.
Examination Report dated Jul. 19, 2019 in European Patent Application No. 17711527.6.
Greenough et al., "Characterization of Family D DNA polymerase from Thermococcus sp. 9°N," Extremophiles. 2014, 18(4), 653-664.
International Search Report and Written Opinion dated Jun. 6, 2017 in PCT Application No. PCT/US2017/020921.
Kankia, "Self-dissociative primers for nucleic acid amplification and detection based on DNA quadruplexes with intrinsic fluorescence," Analytical Biochemistry 2011, 409(1), 59-65.
Krishnan et al., "PCR in a Rayleigh-Bénard Convection Cell," Science 2002, 298(5594), 793.
Lenglet et al., "DNA-Destabilizing Agents as an Alternative Approach for Targeting DNA: Mechanisms of Action and Cellular Consequences," J Nucleic Acids. 2010, Article ID 290935, 17 pp. doi:10.4061/2010/290935.
Liu et al., "Polymerase Spiral Reaction (PSR): A novel isothermal nucleic acid amplification method," Scientific Reports 2015, 5(12723), 1-8.
Mahalanabis et al., "An integrated disposable device for DNA extraction and helicase dependent amplification," Biomed Microdevices 2010, 12(2), 353-359.
Moore, "Alere i Isothermal Amplification," presented at Seventh National Molecular Microbiology Diagnostics Users Group Fall Meeting and Annual Conference, Oct. 11, 2013, http://www.nmgroup.ca/Document/2013/2013_07.pdf.
Motre et al., "Improving isothermal DNA amplification speed for the rapid detection of Mycobacterium tuberculosis," Journal of Microbiological Methods 2011, 84(2), 343-345.
Needham-Vandevanter et al., "Characterization of an adduct between CC-1065 and a defined oligodeoxynucleotide duplex.," Nucleic Acids Res. 1984, 12(15), 6159-6168.
Non-Final Office Action dated Sep. 26, 2016 in U.S. Appl. No. 15/090,405.
Notice of Reasons for Rejection dated Mar. 6, 2020 in Japanese Patent Application No. 2019-503197.
Notice of Allowance dated Dec. 2, 2016 in U.S. Appl. No. 15/090,405.
Pearson and Regnier, "High-performance anion-exchange chromatography of oligonucleotides," Journal of Chromatography A 1983, 255(21), 137-149.
Piepenburg et al., "DNA Detection Using Recombination Proteins," PLoS Biol 2006, 4(7), e204.
Singh et al., "Effect of Different Denaturing Agents on the Detectability of Specific DNA Sequences of Various Base Compositions by in Situ Hybridisation," Chromosoma. 1977;60(4):377-389.
Southworth et al., "Cloning of thermostable DNA polymerases from hyperthermophilic marine Archaea with emphasis on Thermococcus sp. 9 degrees N-7 and mutations affecting 3'-5' exonuclease activity," Proc. Natl. Acad. Sci. USA 1996, 93, 5281-5285.
Tan et al., "Specific versus Nonspecific Isothermal DNA Amplification through Thermophilic Polymerase and Nicking Enzyme Activities," Biochemistry 2008, 47(38), 9987-9999.
Tong et al. "Multiple strategies to improve sensitivity, speed and robustness of isothermal nucleic acid amplification for rapid pathogen detection," BMC Biotechnol. 2011, 11(50), 7 pp.
Tsai et al., "Development of TaqMan Probe-Based Insulated Isothermal PCR (iiPCR) for Sensitive and Specific On-Site Pathogen Detection," PLoS One. 2012, 7(9), e45278.
Tsai et al., "Validation of a Commercial Insulated Isothermal PCR-based POCKIT Test for Rapid and Easy Detection of White Spot Syndrome Virus Infection in Litopenaeus vannamei," PLoS One. 2014, 9(3), e90545.
Tyagi et al., "Molecular Beacons: Probes that Fluoresce upon Hybridization," Nature Biotechnology 1996, 14, 303-308.
Vincent et al., "Helicase-dependent isothermal DNA amplification," EMBO Rep. 2004, 5(8), 795-800.
Wolfe et al., "A genotyping strategy based on incorporation and cleavage of chemically modified nucleotides," Proc Natl Acad Sci U S A 2002, 99(17), 11073-11078.
Xu et al., "Cross Priming Amplification: Mechanism and Optimization for Isothermal DNA Amplification," Sci Rep. 2012, 2(246), 1-7.
Zhao et al., "Isothermal Amplification of Nucleic Acids," Chem. Rev. 2015, 115(22), 12491-12545.
Extended European Search Report dated Oct. 16, 2020 in European Patent Application No. 20182776.3.
Notice of Allowance dated Aug. 3, 2020 in Japanese Patent Application No. 2019-503197.

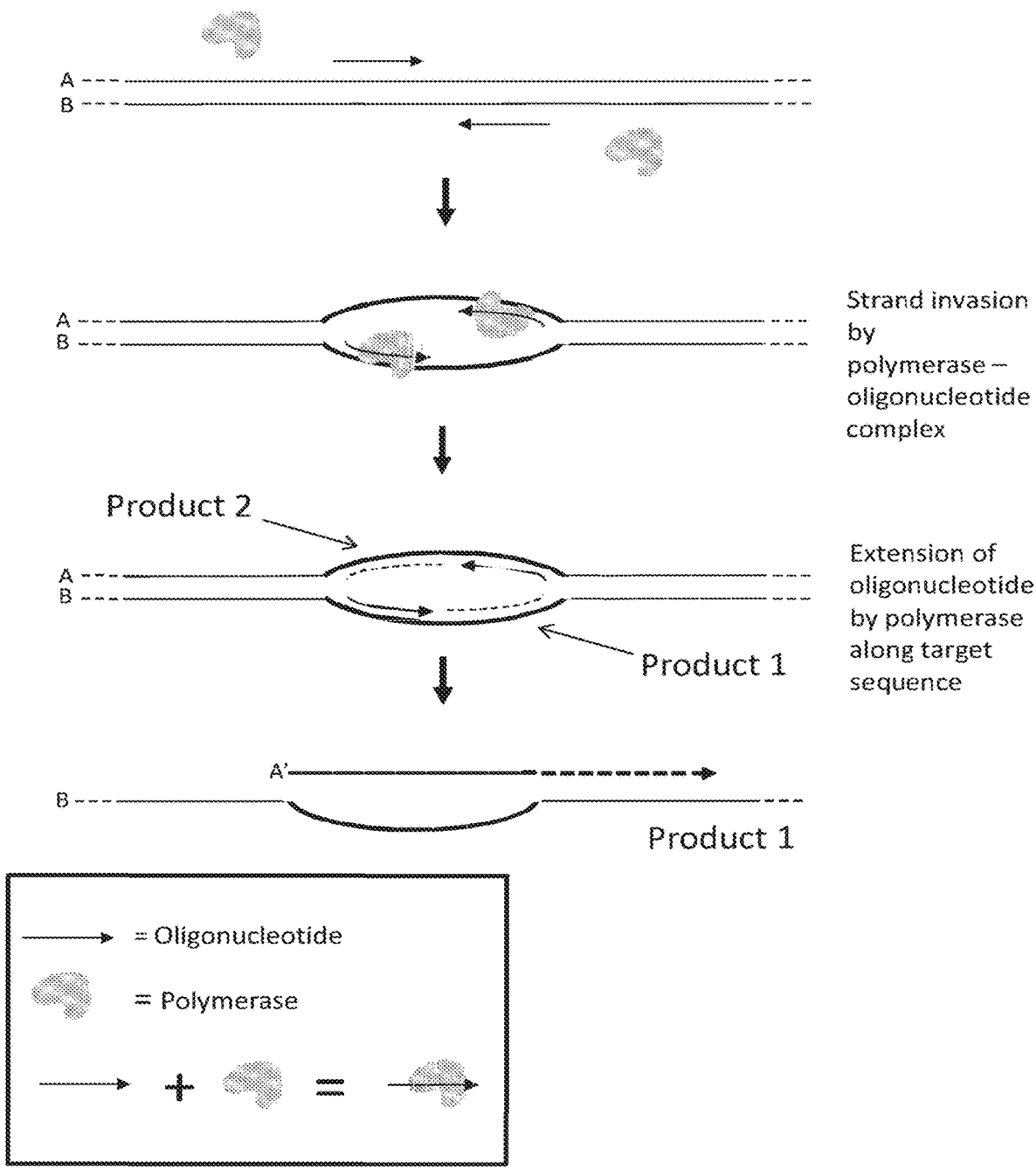

Product 1

Strand invasion by polymerase – oligonucleotide complex

Extension of oligonucleotide by polymerase along target sequence (A' strand) to generate B' strand Product 1'

Strand invasion and extension

Continuous strand invasion and extension

ISOTHERMAL AMPLIFICATION COMPONENTS AND PROCESSES

RELATED PATENT APPLICATIONS

This patent application is continuation of U.S. patent application Ser. No. 16/089,063, filed on Sep. 27, 2018, which is a 35 U.S.C. 371 national phase application of International Patent Cooperation Treaty (PCT) Application No. PCT/US2017/020921, filed on Mar. 6, 2017, entitled ISOTHERMAL AMPLIFICATION COMPONENTS AND PROCESSES, which claims the benefit of U.S. patent application Ser. No. 15/090,405 filed on Apr. 4, 2016, entitled ISOTHERMAL AMPLIFICATION COMPONENTS AND PROCESSES. The entire content of the foregoing applications is incorporated herein by reference, including all text, tables and drawings, for all purposes.

SEQUENCE LISTING

The instant application contains a Sequence Listing which has been submitted electronically in ASCII format and is hereby incorporated by reference in its entirety. Said ASCII copy, created on May 13, 2020, is named Sequence_Listing.txt and is 20 KB in size.

FIELD

The technology relates in part to methods and compositions for isothermal amplification of nucleic acids.

BACKGROUND

Nucleic acid-based diagnostics can be useful for rapid detection of infection, disease and/or genetic variations. For example, identification of bacterial or viral nucleic acid in a sample can be useful for diagnosing a particular type of infection. Other examples include identification of single nucleotide polymorphisms for disease management or forensics, and identification of genetic variations indicative of genetically modified food products. Often, nucleic acid-based diagnostic assays require amplification of a specific portion of nucleic acid in a sample. A common technique for nucleic acid amplification is the polymerase chain reaction (PCR). This technique typically requires a cycling of temperatures (i.e., thermocycling) to proceed through the steps of denaturation (i.e., separation of the strands in the double-stranded DNA (dsDNA) complex), annealing of oligonucleotide primers (short strands of complementary DNA sequences), and extension of the primer along a complementary target by a polymerase. Such thermocycling can be a time consuming process that generally requires specialized machinery. Thus, a need exists for quicker nucleic acid amplification methods that can be performed without thermocycling. Such methods may be useful, for example, for on-site testing and point-of-care diagnostics.

SUMMARY

Provided herein in certain aspects are methods for amplifying nucleic acid, comprising contacting non-denatured sample nucleic acid under isothermal amplification conditions with components comprising a) at least one oligonucleotide, which at least one oligonucleotide comprises a polynucleotide complementary to a target sequence in the sample nucleic acid, and b) at least one component providing hyperthermophile polymerase activity, thereby generating a nucleic acid amplification product.

Also provided herein in certain aspects are methods for amplifying nucleic acid, comprising contacting non-denatured sample nucleic acid under isothermal amplification conditions with a) non-enzymatic components comprising at least one oligonucleotide, which at least one oligonucleotide comprises a polynucleotide complementary to a target sequence in the sample nucleic acid, and b) an enzymatic component consisting of a hyperthermophile polymerase or a polymerase comprising an amino acid sequence that is at least about 90% identical to a hyperthermophile polymerase, thereby generating a nucleic acid amplification product.

Also provided herein in certain aspects are methods for amplifying nucleic acid, comprising contacting non-denatured sample nucleic acid under isothermal amplification conditions with a) non-enzymatic components comprising at least one oligonucleotide, which at least one oligonucleotide comprises a polynucleotide complementary to a target sequence in the sample nucleic acid, and b) enzymatic activity consisting of i) hyperthermophile polymerase activity and, optionally, ii) reverse transcriptase activity, thereby generating a nucleic acid amplification product.

Also provided herein in certain aspects are methods for processing nucleic acid, comprising amplifying nucleic acid, where the amplifying consists essentially of contacting non-denatured sample nucleic acid under isothermal amplification conditions with a) at least one oligonucleotide, which at least one oligonucleotide comprises a polynucleotide complementary to a target sequence in the sample nucleic acid, and b) at least one component providing hyperthermophile polymerase activity, thereby generating a nucleic acid amplification product.

Also provided herein in certain aspects are methods for processing nucleic acid, comprising amplifying nucleic acid, where the amplifying consists essentially of contacting non-denatured sample nucleic acid under isothermal amplification conditions with a) non-enzymatic components comprising at least one oligonucleotide, which at least one oligonucleotide comprises a polynucleotide complementary to a target sequence in the sample nucleic acid, and b) an enzymatic component consisting of a hyperthermophile polymerase or a polymerase comprising an amino acid sequence that is at least about 90% identical to a hyperthermophile polymerase, thereby generating a nucleic acid amplification product.

Also provided herein in certain aspects are methods for processing nucleic acid, comprising amplifying nucleic acid, where the amplifying consists essentially of contacting non-denatured sample nucleic acid under isothermal amplification conditions with a) non-enzymatic components comprising at least one oligonucleotide, which at least one oligonucleotide comprises a polynucleotide complementary to a target sequence in the sample nucleic acid, and b) enzymatic activity consisting of i) hyperthermophile polymerase activity and, optionally, ii) reverse transcriptase activity, thereby generating a nucleic acid amplification product.

Also provided herein in certain aspects are methods for processing nucleic acid, comprising amplifying nucleic acid, where the amplifying consists of contacting non-denatured sample nucleic acid under isothermal amplification conditions with a) at least one oligonucleotide, which at least one oligonucleotide comprises a polynucleotide complementary to a target sequence in the sample nucleic acid, and b) at least one component providing hyperthermophile polymerase activity, thereby generating a nucleic acid amplification product.

Also provided herein in certain aspects are methods for processing nucleic acid, comprising amplifying nucleic acid, where the amplifying consists of contacting non-denatured sample nucleic acid under isothermal amplification conditions with a) non-enzymatic components comprising at least one oligonucleotide, which at least one oligonucleotide comprises a polynucleotide complementary to a target sequence in the sample nucleic acid, and b) an enzymatic component consisting of a hyperthermophile polymerase or a polymerase comprising an amino acid sequence that is at least about 90% identical to a hyperthermophile polymerase, thereby generating a nucleic acid amplification product.

Also provided herein in certain aspects are methods for processing nucleic acid, comprising amplifying nucleic acid, where the amplifying consists of contacting non-denatured sample nucleic acid under isothermal amplification conditions with a) non-enzymatic components comprising at least one oligonucleotide, which at least one oligonucleotide comprises a polynucleotide complementary to a target sequence in the sample nucleic acid, and b) enzymatic activity consisting of i) hyperthermophile polymerase activity and, optionally, ii) reverse transcriptase activity, thereby generating a nucleic acid amplification product.

Also provided herein in certain aspects are methods for determining the presence, absence or amount of a target sequence in sample nucleic acid, comprising a) amplifying a target sequence in the sample nucleic acid, where the target sequence comprises a first strand and a second strand, the first strand and second strand are complementary to each other, and the amplifying comprises contacting non-denatured sample nucleic acid under helicase-free and/or recombinase-free isothermal amplification conditions with i) a first oligonucleotide and a second oligonucleotide, where the first oligonucleotide comprises a first polynucleotide continuously complementary to a sequence in the first strand, and the second oligonucleotide comprises a second polynucleotide continuously complementary to a sequence in the second strand; and ii) at least one component providing a hyperthermophile polymerase activity, thereby generating a nucleic acid amplification product, where the nucleic acid amplification product comprises 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases, and the spacer sequence is flanked by the first nucleotide sequence and the second nucleotide sequence; and b) detecting the nucleic acid amplification product, where detecting the nucleic acid amplification product comprises use of a real-time detection method and is performed in 10 minutes or less from the time the sample nucleic acid is contacted with (a)(i) and (a)(ii), whereby the presence, absence or amount of a target sequence in sample nucleic acid is determined.

Also provided herein in certain aspects are methods for determining the presence, absence or amount of a target sequence in sample nucleic acid, comprising a) amplifying a target sequence in the sample nucleic acid, which target sequence comprises a first strand and a second strand, which first strand and second strand are complementary to each other, where the amplifying comprises contacting non-denatured sample nucleic acid under helicase-free and/or recombinase-free isothermal amplification conditions with i) a first oligonucleotide and a second oligonucleotide, where the first oligonucleotide consists of a first polynucleotide continuously complementary to a sequence in the first strand, and the second oligonucleotide consists of a second polynucleotide continuously complementary to a sequence in the second strand; and ii) at least one component providing a hyperthermophile polymerase activity, thereby generating a nucleic acid amplification product, where the nucleic acid amplification product consists of 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases, where the spacer sequence is flanked by the first nucleotide sequence and the second nucleotide sequence; and b) detecting the nucleic acid amplification product, where detecting the nucleic acid amplification product comprises use of a real-time detection method and is performed in 10 minutes or less from the time the sample nucleic acid is contacted with (a)(i) and (a)(ii), whereby the presence, absence or amount of a target sequence in sample nucleic acid is determined.

Also provided herein in certain aspects are kits for determining the presence, absence or amount of a target sequence in sample nucleic acid comprising a) components for amplifying a target sequence in the sample nucleic acid under helicase-free and/or recombinase-free isothermal amplification conditions, which components comprise i) a first oligonucleotide and a second oligonucleotide, where the first oligonucleotide comprises a first polynucleotide continuously complementary to a sequence in a first strand of the target sequence, and the second oligonucleotide comprises a second polynucleotide continuously complementary to a sequence in a second strand of the target sequence, which first strand and second strand of the target sequence are complementary to each other; and ii) at least one component providing a hyperthermophile polymerase activity; and b) at least one component providing real-time detection activity for a nucleic acid amplification product.

Also provided herein in certain aspects are kits for determining the presence, absence or amount of a target sequence in sample nucleic acid comprising a) components for amplifying a target sequence in the sample nucleic acid under helicase-free and/or recombinase-free isothermal amplification conditions, which components comprise i) a first oligonucleotide and a second oligonucleotide, where the first oligonucleotide consists of a first polynucleotide continuously complementary to a sequence in a first strand of the target sequence, and the second oligonucleotide consists of a second polynucleotide continuously complementary to a sequence in a second strand of the target sequence, which first strand and second strand of the target sequence are complementary to each other; and ii) at least one component providing a hyperthermophile polymerase activity; and b) at least one component providing real-time detection activity for a nucleic acid amplification product.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 1:
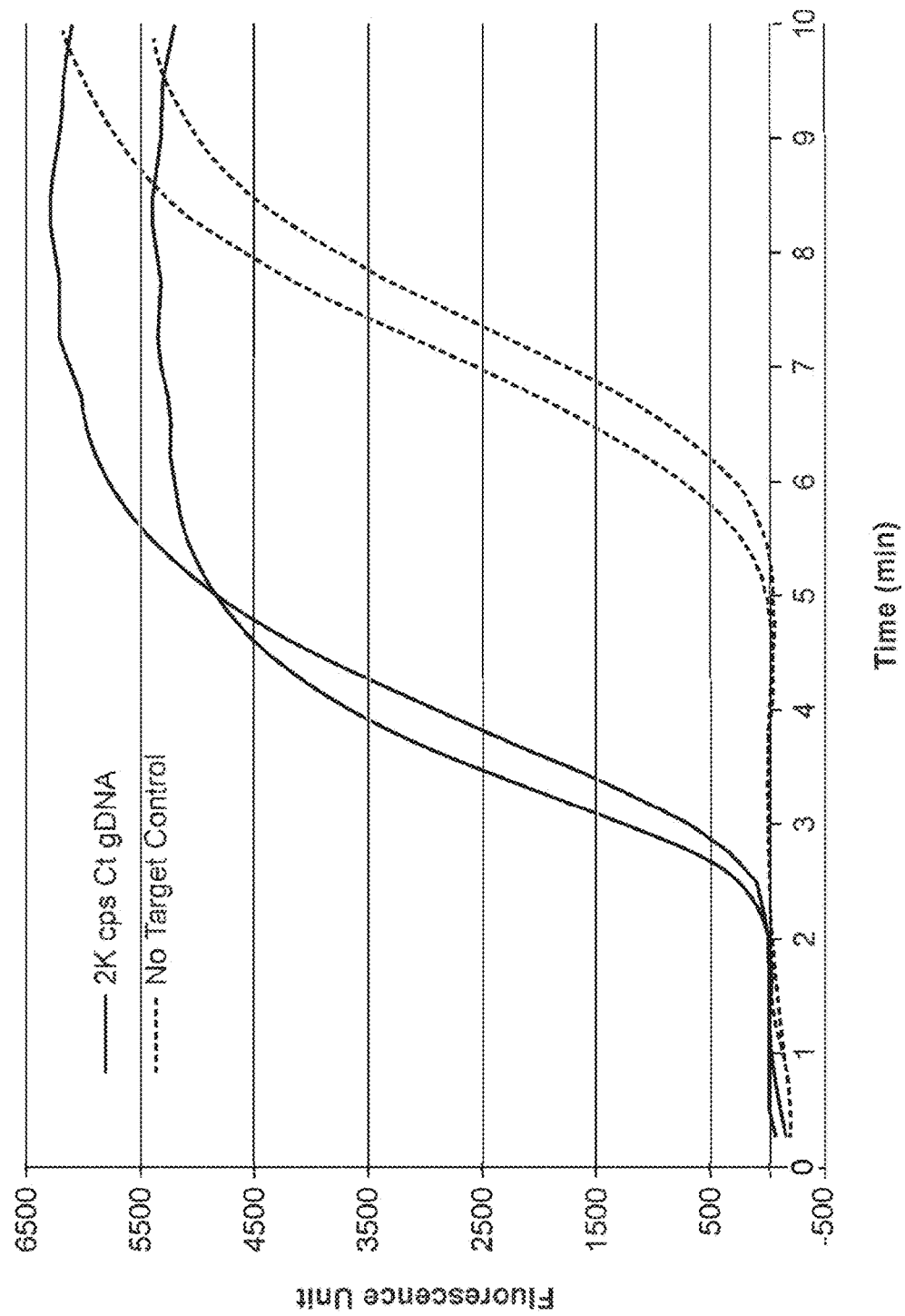
FIG. 1 shows real-time detection of chlamydia genomic DNA amplification reactions performed in duplicate with dH$_2$O or Tris-EDTA buffer (TE) used as a no target control (NTC; negative control).

Provided herein are methods and compositions for amplifying nucleic acid. Traditional nucleic acid amplification methods typically require a thermocycling process, nucleic acid denaturation, proteins (e.g., enzymes) that promote strand unwinding, strand separation and/or strand exchange (e.g., helicases, recombinases), and/or endonuclease agents (e.g., restriction enzymes, nicking enzymes), and often require a minimum reaction time of 20 to 30 minutes. The nucleic acid amplification methods provided herein can be performed without thermocycling, without nucleic acid denaturation, without added proteins (e.g., enzymes) to promote strand unwinding, strand separation and/or strand exchange, without endonuclease agents, and within a reaction time of 10 minutes.

Nucleic Acid, Subjects, Samples and Nucleic Acid Processing

Provided herein are methods and compositions for amplifying nucleic acid. The terms "nucleic acid" and "nucleic acid molecule" may be used interchangeably herein. The terms refer to nucleic acids of any composition, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus, a mitochondria, or cytoplasm of a cell in certain embodiments. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid may be used interchangeably with locus, gene, cDNA, and mRNA encoded by a gene. The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame, "forward" strand or "reverse" strand) and double-stranded polynucleotides. The term "gene" means the segment of DNA involved in producing a polypeptide chain; and generally includes regions preceding and following the coding region (leader and trailer) involved in the transcription/translation of the gene product and the regulation of the transcription/translation, as well as intervening sequences (introns) between individual coding segments (exons). A nucleotide or base generally refers to the purine and pyrimidine molecular units of nucleic acid (e.g., adenine (A), thymine (T), guanine (G), and cytosine (C)). For RNA, the base thymine is replaced with uracil. Nucleic acid length or size may be expressed as a number of bases.

In some embodiments of the methods provided herein, one or more nucleic acid targets are amplified. Target nucleic acids may be referred to as target sequences, target polynucleotides, and/or target polynucleotide sequences, and may include double-stranded and single-stranded nucleic acid molecules. Target nucleic acid may be, for example, DNA or RNA. Where the target nucleic acid is an RNA molecule, the molecule may be, for example, double-stranded, single-stranded, or the RNA molecule may comprise a target sequence that is single-stranded. Where the target nucleic acid is double stranded, the target nucleic acid generally includes a first strand and a second strand. A first strand and a second strand may be referred to as a forward strand and a reverse strand and generally are complementary to each other. Where the target nucleic acid is single stranded, a complementary strand may be generated, for example by polymerization and/or reverse transcription, rendering the target nucleic acid double stranded and having a first/forward strand and a second/reverse strand.

A target sequence may refer to either the sense or antisense strand of a nucleic acid sequence, and also may refer to sequences as they exist on target nucleic acids, amplified copies, or amplification products, of the original target sequence. A target sequence may be a subsequence within a larger polynucleotide. For example, a target sequence may be a short sequence (e.g., 20 to 50 bases) within a nucleic acid fragment, a chromosome, a plasmid, that is targeted for amplification. In some embodiments, a target sequence may refer to a sequence in a target nucleic acid that is complementary to an oligonucleotide (e.g., primer) used for amplifying a nucleic acid. Thus, a target sequence may refer to the entire sequence targeted for amplification or may refer to a subsequence in the target nucleic acid where an oligonucleotide binds. An amplification product may be a larger molecule that comprises the target sequence, as well as at least one other sequence, or other nucleotides. In some embodiments, an amplification product is about the same length as the target sequence. In some embodiments, an amplification product is exactly the same length as the target sequence. In some embodiments, an amplification product comprises the target sequence. In some embodiments, an amplification product consists of the target sequence.

The length of the target sequence, and/or the guanosine cytosine (GC) concentration (percent), may depend, in part, on the temperature at which an amplification reaction is run, and this temperature may depend, in part, on the stability of the polymerase(s) used in the reaction. Sample assays may be performed to determine an appropriate target sequence length and GC concentration for a set of reaction conditions. For example, where a polymerase is stable up to 60° C. to 65° C., then the target sequence may be, for example, from 19 to 50 nucleotides in length, or for example, from about 40 to 50, 20 to 45, 20 to 40, or 20 to 30 nucleotides in length. GC concentration under these conditions may be, for example, less than 60%, less than 55%, less than 50%, or less than 45%.

Target nucleic acid may include, for example, genomic nucleic acid, plasmid nucleic acid, mitochondrial nucleic acid, cellular nucleic acid, extracellular nucleic acid, bacterial nucleic acid and viral nucleic acid. In some embodiments, target nucleic acid may include genomic DNA, chromosomal DNA, plasmid DNA, mitochondrial DNA, a gene, any type of cellular RNA, messenger RNA, bacterial RNA, viral RNA or a synthetic oligonucleotide. Genomic nucleic acid may include any nucleic acid from any genome, for example, including animal, plant, insect, viral and bacterial genomes, including, for example, genomes present in spores. In some embodiments, genomic target nucleic acid may be within a particular genomic locus or a plurality of genomic loci. A genomic locus may include any or a combination of open reading frame DNA, non-transcribed DNA, intronic sequences, extronic sequences, promoter sequences, enhancer sequences, flanking sequences, or any sequences considered associated with a given genomic locus.

In some embodiments, a target sequence comprises one or more repetitive elements (e.g., multiple repeat sequences, inverted repeat sequences, palindromic sequences, tandem repeats, microsatellites, minisatellites, and the like). In some embodiments, a target sequence is present within a sample nucleic acid (e.g., within a nucleic acid fragment, a chromosome, a genome, a plasmid) as a repetitive element (e.g., a multiple repeat sequence, an inverted repeat sequence, a palindromic sequence, a tandem repeat, a microsatellite repeat, a minisatellite repeat and the like). For example, a target sequence may occur multiple times as a repetitive element and one, some, or all occurrences of the target sequence within a repetitive element may be amplified (e.g., using a single pair of primers) using methods described herein. In some embodiments, a target sequence is present within a sample nucleic acid (e.g., within a nucleic acid fragment, a chromosome, a genome, a plasmid) as a duplication and/or a paralog.

Target nucleic acid may include microRNAs. MicroRNAs, miRNAs, or small temporal RNAs (stRNAs) are short (e.g., about 21 to 23 nucleotides long) and single-stranded RNA sequences involved in gene regulation. MicroRNAs may interfere with translation of messenger RNAs and are partially complementary to messenger RNAs. Target nucleic acid may include microRNA precursors such as primary transcript (pri-miRNA) and pre-miRNA stem-loop-structured RNA that is further processed into miRNA. Target nucleic acid may include short interfering RNAs (siRNAs), which are short (e.g., about 20 to 25 nucleotides long) and at least partially double-stranded RNA molecules involved in RNA interference (e.g., down-regulation of viral replication or gene expression).

Nucleic acid utilized in methods described herein may be obtained from any suitable biological specimen or sample, and often is isolated from a sample obtained from a subject. A subject can be any living or non-living organism, including but not limited to a human, a non-human animal, a plant, a bacterium, a fungus, a virus, or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female, and a subject may be any age (e.g., an embryo, a fetus, infant, child, adult).

A sample or test sample can be any specimen that is isolated or obtained from a subject or part thereof. Non-limiting examples of specimens include fluid or tissue from a subject, including, without limitation, blood or a blood product (e.g., serum, plasma, or the like), umbilical cord blood, bone marrow, chorionic villi, amniotic fluid, cerebrospinal fluid, spinal fluid, lavage fluid (e.g., bronchoalveolar, gastric, peritoneal, ductal, ear, arthroscopic), biopsy sample, celocentesis sample, cells (e.g., blood cells) or parts thereof (e.g., mitochondrial, nucleus, extracts, or the like), washings of female reproductive tract, urine, feces, sputum, saliva, nasal mucous, prostate fluid, lavage, semen, lymphatic fluid, bile, tears, sweat, breast milk, breast fluid, hard tissues (e.g., liver, spleen, kidney, lung, or ovary), the like or combinations thereof. The term blood encompasses whole blood, blood product or any fraction of blood, such as serum, plasma, buffy coat, or the like as conventionally defined. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation.

A sample or test sample can include samples containing spores, viruses, cells, nucleic acid from prokaryotes or eukaryotes, or any free nucleic acid. For example, a method described herein may be used for detecting nucleic acid on the outside of spores (e.g., without the need for lysis). A sample may be isolated from any material suspected of containing a target sequence, such as from a subject described above. In certain instances, a target sequence may be present in air, plant, soil, or other materials suspected of containing biological organisms.

Nucleic acid may be derived (e.g., isolated, extracted, purified) from one or more sources by methods known in the art. Any suitable method can be used for isolating, extracting and/or purifying nucleic acid from a biological sample, non-limiting examples of which include methods of DNA preparation in the art, and various commercially available reagents or kits, such as Qiagen's QIAamp Circulating Nucleic Acid Kit, QiaAmp DNA Mini Kit or QiaAmp DNA Blood Mini Kit (Qiagen, Hilden, Germany), GenomicPrep™ Blood DNA Isolation Kit (Promega, Madison, Wis.), GFX™ Genomic Blood DNA Purification Kit (Amersham, Piscataway, N.J.), and the like or combinations thereof.

In some embodiments, a cell lysis procedure is performed. Cell lysis may be performed prior to initiation of an amplification reaction described herein (e.g., to release DNA and/or RNA from cells for amplification). Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract nucleic acids from the cells, followed by treatment with chaotropic salts. In some embodiments, cell lysis comprises use of detergents (e.g., ionic, nonionic, anionic, zwitterionic). In some embodiments, cell lysis comprises use of ionic detergents (e.g., sodium dodecyl sulfate (SDS), sodium lauryl sulfate (SLS), deoxycholate, cholate, sarkosyl) Physical methods such as freeze/thaw followed by grinding, the use of cell presses and the like also may be useful. High salt lysis procedures also may be used. For example, an alkaline lysis procedure may be utilized. The latter procedure traditionally incorporates the use of phenol-chloroform solutions, and an alternative phenol-chloroform-free procedure involving three solutions may be utilized. In the latter procedures, one solution can contain 15 mM Tris, pH 8.0; 10 mM EDTA and 100 μg/ml Rnase A; a second solution can contain 0.2N NaOH and 1% SDS; and a third solution can contain 3M KOAc, pH 5.5, for example. In some embodiments, a cell lysis buffer is used in conjunction with the methods and components described herein.

Nucleic acid may be provided for conducting methods described herein without processing of the sample(s) containing the nucleic acid, in certain embodiments. For example, in some embodiments, nucleic acid is provided for conducting amplification methods described herein without prior nucleic acid purification. In some embodiments, a target sequence is amplified directly from a sample (e.g., without performing any nucleic acid extraction, isolation, purification and/or partial purification steps). In some embodiments, nucleic acid is provided for conducting methods described herein after processing of the sample(s) containing the nucleic acid. For example, a nucleic acid can be extracted, isolated, purified, or partially purified from the sample(s). The term "isolated" generally refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" can refer to a nucleic acid removed from a subject (e.g., a human subject). An isolated nucleic acid can be provided with fewer non-nucleic acid components (e.g., protein, lipid, carbohydrate) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" generally refers to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components.

Nucleic acid may be provided for conducting methods described herein without modifying the nucleic acid. Modifications may include, for example, denaturation, digestion, nicking, unwinding, incorporation and/or ligation of heterogeneous sequences, addition of epigenetic modifications, addition of labels (e.g., radiolabels such as $^{32}$P, 33P, $^{125}$I, or $^{35}$S; enzyme labels such as alkaline phosphatase; fluorescent labels such as fluorescein isothiocyanate (FITC); or other labels such as biotin, avidin, digoxigenin, antigens, haptens, fluorochromes), and the like. Accordingly, in some embodiments, an unmodified nucleic acid is amplified.

Amplification

Provided herein are methods for amplifying nucleic acid. In some embodiments, nucleic acids are amplified using a suitable amplification process. Nucleic acid amplification typically involves enzymatic synthesis of nucleic acid amplicons (copies), which contain a sequence complementary to a nucleotide sequence being amplified. In some embodiments, an amplification method is performed in a single vessel, a single chamber, and/or a single volume (i.e., contiguous volume). In some embodiments, an amplification method and a detection method (e.g., such as a detection method described herein) are performed in a single vessel, a single chamber, and/or a single volume (i.e., contiguous volume).

The terms "amplify", "amplification", "amplification reaction", or "amplifying" refer to any in vitro process for multiplying the copies of a target nucleic acid. Amplification sometimes refers to an "exponential" increase in target nucleic acid. However, "amplifying" may also refer to linear increases in the numbers of a target nucleic acid, but is different than a one-time, single primer extension step. In some embodiments a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may limit inaccuracies associated with depleted reactants in certain amplification reactions, and also may reduce amplification biases due to nucleotide sequence or species abundance of the target. In some embodiments a one-time primer extension may be performed as a prelude to linear or exponential amplification.

A generalized description of an amplification process is presented herein. Primers (e.g., oligonucleotides described herein) and target nucleic acid are contacted, and complementary sequences anneal or hybridize to one another, for example. Primers can anneal to a target nucleic acid, at or near (e.g., adjacent to, abutting, and the like) a sequence of interest. A primer annealed to a target may be referred to as a primer-target hybrid, hybridized primer-target, or a primer-target duplex. The terms near or adjacent to when referring to a nucleotide sequence of interest refer to a distance (e.g., number of bases) or region between the end of the primer and the nucleotide or nucleotides (e.g., nucleotide sequence) of a target. Generally, adjacent is in the range of about 1 nucleotide to about 50 nucleotides (e.g., 1 nucleotide, 2 nucleotides, 3 nucleotides, 4 nucleotides, 5 nucleotides, 6 nucleotides, 7 nucleotides, 8 nucleotides, 9 nucleotides, about 10 nucleotides, about 20 nucleotides, about 30 nucleotides, about 40 nucleotides, about 50 nucleotides) away from a nucleotide or nucleotide sequence of interest. In some embodiments, primers in a set (e.g., a pair of primers, a forward and a reverse primer, a first oligonucleotide and a second oligonucleotide) anneal within about 1 to 20 nucleotides from a nucleotide or nucleotide sequence of interest and produce amplified products. In some embodiments, primers anneal within a nucleotide or a nucleotide sequence of interest. After annealing, each primer is extended along the target (i.e., template strand) by a polymerase to generate a complementary strand. Several cycles of primer annealing and extension may be carried out, for example, until a detectable amount of amplification product is generated. In some embodiments, where a target nucleic acid is RNA, a DNA copy (cDNA) of the target RNA may be synthesized prior to or during the amplification step by reverse transcription.

Components of an amplification reaction may include, for example, one or more primers (e.g., individual primers, primer pairs, primer sets, oligonucleotides, multiple primer sets for multiplex amplification, and the like), nucleic acid target(s) (e.g., target nucleic acid from a sample), one or more polymerases, nucleotides (e.g., dNTPs and the like), and a suitable buffer (e.g., a buffer comprising a detergent, a reducing agent, monovalent ions, and divalent ions). An amplification reaction may further include a reverse transcriptase, in some embodiments. An amplification reaction may further include one or more detection agents, such as one or more of the detection agents described herein, in some embodiments. In some embodiments, components of an amplification reaction consist of primers, target nucleic acid, a polymerase, nucleotides, and a suitable buffer. In some embodiments, components of an amplification reaction consist of primers, target nucleic acid, a polymerase, a reverse transcriptase, nucleotides, and a suitable buffer. In some embodiments, components of an amplification reaction consist of primers, target nucleic acid, a polymerase, a detection agent, nucleotides, and a suitable buffer. In some embodiments, components of an amplification reaction consist of primers, target nucleic acid, a polymerase, a reverse transcriptase, a detection agent, nucleotides, and a suitable buffer. In some embodiments, components of an amplification reaction consist essentially of primers, target nucleic acid, a polymerase, nucleotides, and a suitable buffer. In some embodiments, components of an amplification reaction consist essentially of primers, target nucleic acid, a polymerase, a reverse transcriptase, nucleotides, and a suitable buffer. In some embodiments, components of an amplification reaction consist essentially of primers, target nucleic acid, a polymerase, a detection agent, nucleotides, and a suitable buffer. In some embodiments, components of an amplification reaction consist essentially of primers, target nucleic acid, a polymerase, a reverse transcriptase, a detection agent, nucleotides, and a suitable buffer. When components of an amplification reaction consist essentially of certain components, additional components or features may be included that do not have a significant effect on the amplification and/or are not necessary for generating a detectable product. For example, additional components or features may be included that do not have a significant effect on the ability of the components and conditions herein to achieve amplification under isothermal conditions and generate a detectable amplification product within about 10 minutes or less. Such additional components or features may be referred to as non-essential components and may include typical reaction components and/or common additives such as salts, buffers, detergents, ions, oils, proteins, polymers and the like.

Nucleic acid amplification may be conducted in the presence of native nucleotides, such as, for example, dideoxyribonucleoside triphosphates (dNTPs), and/or derivatized nucleotides. A native nucleotide generally refers to adenylic acid, guanylic acid, cytidylic acid, thymidylic acid, or uridylic acid. A derivatized nucleotide generally is a nucleotide other than a native nucleotide. Nucleotides typically are designated as follows. A ribonucleoside triphosphate is referred to as NTP or rNTP, where N can be A, G, C, U. A deoxynucleoside triphosphate substrates is referred to as dNTP, where N can be A, G, C, T, or U. Monomeric nucleotide subunits may be denoted as A, G, C, T, or U herein with no particular reference to DNA or RNA. In some embodiments, non-naturally occurring nucleotides or nucleotide analogs, such as analogs containing a detectable label (e.g., fluorescent or colorimetric label), may be used. For example, nucleic acid amplification may be carried out in the presence of labeled dNTPs, such as, for example, radiolabels such as $^{32}P$, $^{33}P$, $^{125}I$, or $^{35}S$; enzyme labels such as alkaline phosphatase; fluorescent labels such as fluorescein isothiocyanate (FITC); or other labels such as biotin, avidin, digoxigenin, antigens, haptens, or fluorochromes. In some embodiments, nucleic acid amplification may be carried out in the presence of modified dNTPs, such as, for example, heat activated dNTPs (e.g., CleanAmp™ dNTPs from TriLink).

In some embodiments, components of an amplification reaction may include non-enzymatic components and enzymatic components. Non-enzymatic components may include, for example, primers, nucleotides, buffers, salts, reducing agents, detergents, and ions; and generally do not include proteins (e.g., nucleic acid binding proteins), enzymes, or proteins having enzymatic activity such as, for example, polymerases, reverse transcriptases, helicases, topoisomerases, ligases, exonucleases, endonucleases, restriction enzymes, nicking enzymes, recombinases and the like. In some embodiments, an enzymatic component may consist of a polymerase or may consist of a polymerase and a reverse transcriptase. Accordingly, such enzymatic components would exclude other proteins (e.g., nucleic acid binding proteins and/or proteins having enzymatic activity) such as, for example, helicases, topoisomerases, ligases, exonucleases, endonucleases, restriction enzymes, nicking enzymes, recombinases, and the like.

In some embodiments, amplification conditions comprise an enzymatic activity. Typically, an enzymatic activity is provided by a polymerase, and in certain instances, an enzymatic activity is provided by a polymerase and a reverse transcriptase. In some embodiments, an enzymatic activity consists of a polymerase activity. In some embodiments, an enzymatic activity consists of a polymerase activity and a reverse transcriptase activity. Accordingly, in some embodiments, enzymatic activity does not include enzymatic activity provided by other enzymes such as, for example, helicases, topoisomerases, ligases, exonucleases, endonucleases, restriction enzymes, nicking enzymes, recombinases, and the like. In certain instances, a polymerase activity and a reverse transcriptase activity are provided by separate enzymes or separate enzyme types (e.g., polymerase(s) and reverse transcriptase(s)). In certain instances, a polymerase activity and a reverse transcriptase activity are provided by a single enzyme or enzyme type (e.g., polymerase(s)).

In some embodiments, amplification of nucleic acid comprises a non-thermocycling type of polymerase chain reaction (PCR). In some embodiments, amplification of nucleic acid comprises an isothermal amplification process. In some embodiments, amplification of nucleic acid comprises an isothermal polymerase chain reaction (iPCR). Isothermal amplification generally is an amplification process performed at a constant temperature. Terms such as isothermal conditions, isothermally and constant temperature generally refer to reaction conditions where the temperature of the reaction is kept essentially constant during the course of the amplification reaction. Isothermal amplification conditions generally do not include a thermocycling (i.e., cycling between an upper temperature and a lower temperature) component in the amplification process. When amplifying under isothermal conditions, the reaction may be kept at an essentially constant temperature, which means the temperature may not be maintained at precisely one temperature. For example, small fluctuations in temperature (e.g., ±1 to 5 degrees Celsius) may occur in an isothermal amplification process due to, for example, environmental or equipment-based variables. Often, the entire reaction volume is kept at an essentially constant temperature, and isothermal reactions herein generally do not include amplification conditions that rely on a temperature gradient generated within a reaction vessel and/or convective-flow based temperature cycling.

Isothermal amplification reactions herein may be conducted at an essentially constant temperature. In some embodiments, isothermal amplification reactions herein are conducted at a temperature of about 55 degrees Celsius to a temperature of about 75 degrees Celsius. For example, isothermal amplification reactions herein may be conducted at a temperature of about 55 degrees Celsius, about 56 degrees Celsius, about 57 degrees Celsius, about 58 degrees Celsius, about 59 degrees Celsius, about 60 degrees Celsius, about 61 degrees Celsius, about 62 degrees Celsius, about 63 degrees Celsius, about 64 degrees Celsius, about 65 degrees Celsius, about 66 degrees Celsius, about 67 degrees Celsius, about 68 degrees Celsius, about 69 degrees Celsius, about 70 degrees Celsius, about 71 degrees Celsius, about 72 degrees Celsius, about 73 degrees Celsius, about 74 degrees Celsius, or about 75 degrees Celsius. In some embodiments, isothermal amplification reactions herein are conducted at a temperature of about 55 degrees Celsius to a temperature of about 65 degrees Celsius. For example, isothermal amplification reactions herein may be conducted at a temperature of about 60 degrees Celsius. Isothermal amplification reactions herein may be conducted at a temperature of about 65 degrees Celsius. In some embodiments, a temperature element (e.g., heat source) is kept at an essentially constant temperature. In some embodiments, a temperature element is kept at an essentially constant temperature at or below about 75 degrees Celsius. In some embodiments, a temperature element is kept at an essentially constant temperature at or below about 70 degrees Celsius. In some embodiments, a temperature element is kept at an essentially constant temperature at or below about 65 degrees Celsius. In some embodiments, a temperature element is kept at an essentially constant temperature at or below about 60 degrees Celsius.

An amplification process herein may be conducted over a certain length of time. In some embodiments, an amplification process is conducted until a detectable nucleic acid amplification product is generated. A nucleic acid amplification product may be detected by any suitable detection process and/or a detection process described herein. In some embodiments, an amplification process is conducted over a length of time within about 20 minutes or less. For example, an amplification process may be conducted within about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes. In some embodiments, an amplification process is conducted over a length of time within about 10 minutes or less.

Nucleic acid targets may be amplified without exposure to agents or conditions that denature nucleic acid, in some embodiments. Agents or conditions that denature nucleic acid may include agents or conditions that promote strand separation and/or promote unwinding. Nucleic acid targets may be amplified without exposure to agents or conditions that promote strand separation, in some embodiments. Nucleic acid targets may be amplified without exposure to agents or conditions that promote unwinding, in some embodiments. In some embodiments, a target nucleic acid is considered non-denatured if it has not been exposed to agents or conditions that denature nucleic acid and/or promote strand separation and/or promote unwinding prior to or during amplification. Agents or conditions that denature nucleic acid and/or promote strand separation and/or promote unwinding may include, for example, thermal conditions (e.g., high temperatures), pH conditions (e.g., high or low pH), chemical agents, proteins (e.g., enzymatic agents), and the like.

Nucleic acid targets may be amplified without exposure to agents or conditions that denature nucleic acid, in some embodiments. Nucleic acid denaturation, or melting, is the process by which double-stranded nucleic acid unwinds and separates into single strands. Agents and conditions that can promote nucleic acid denaturation include, for example, heat, high pH, low pH, and denaturing agents (e.g., formamide) combined with heat. In some instances, denaturation can be achieved by heating a solution containing nucleic acid to a certain temperature, for example a temperature above 75 degrees Celsius, above 80 degrees Celsius, above 90 degrees Celsius, above 95 degrees Celsius, or higher. In some instances, denaturation can be achieved by exposure to denaturing agents, such as, for example NaOH, HCl, and formamide combined with heat. Specific methods for DNA denaturation are described, for example, in Singh et al., (1977) Chomosoma 60:377-389.

Nucleic acid targets may be amplified without exposure to agents or conditions that promote strand separation and/or unwinding, in some embodiments. For example, nucleic acid targets may be amplified without exposure to a helicase. Helicases are enzymes capable of unwinding and separating double-stranded nucleic acid into single strands. Examples of helicases include human DNA helicases (and their equivalents in other organisms) such as DNA helicase Q1, Bloom syndrome protein, Werner syndrome protein, DNA helicase Q4, DNA helicase Q5, DNA helicase 2 subunit 1, MCM2, MCM3, MCM, MCM5, MCM6, MCM7, MCM8, MCM9, MCM10, Nucleolin, CHD2, CHD7, XPB, XPD, lymphoid-specific helicase, hINO, RuvB-like 1, RuvB-like 2, PIF1, Twinkle, $BACH_1$, RecQ5 alpha, RecQ5 beta, RecQ5 gamma and RTEL1; human RNA helicases (and their equivalents in other organisms) such as RNA helicase DDX1, RNA helicase elF4A-1, RNA helicase elF4A-2, RNA helicase DDX3X, RNA helicase DDX3Y, RNA helicase DDX4, RNA helicase DDX5, RNA helicase DDX6, RNA helicase DHX8, RNA helicase A, RNA helicase DDX10, RNA helicase DDX11, RNA helicase DDX12, Helicase SKI2W, RNA helicase DHX15, RNA helicase DHX16, RNA helicase DDX17, RNA helicase DDX18, RNA helicase DDX19A, RNA helicase DDX19B, RNA helicase DDX20, Nucleolar RNA helicase 2, RNA helicase DDX23, RNA helicase DDX24, RNA helicase DDX25, RNA helicase DDX27, RNA helicase DDX28, RNA helicase DHX29, RNA helicase DHX30, RNA helicase DDX31, RNA helicase DHX32, RNA helicase DHX33, RNA helicase DHX34, RNA helicase DHX35, RNA helicase DHX36, RNA helicase DHX37, RNA helicase PRP 16, RNA helicase DDX39, RNA helicase DHX40, RNA helicase DDX41, RNA helicase DDX42, RNA helicase DDX43, RNA helicase DDX46, RNA helicase DDX47, RNA helicase elF4A-3, RNA helicase DDX49, RNA helicase DDX50, RNA helicase DDX51, RNA helicase DDX52, RNA helicase DDX53, RNA helicase DDX54, RNA helicase DDX55, RNA helicase DDX56, RNA helicase DHX57, RNA helicase DDX58, RNA helicase DHX58, RNA helicase DDX59, RNA helicase DDX60, Spliceosome RNA helicase BAT1, U5.snRNP 200 kDa helicase, Transcriptional regulator ATRX helicase, RNA helicase SUPV3L1, mitochondrial Superkiller viralicidic activity 2-like 2, and Fanconi anemia group J protein; and commercially available helicases. Amplification conditions that do not include use of a helicase may be referred to herein as helicase-free amplification conditions.

In some embodiments, nucleic acid targets may be amplified without exposure to a recombinase. Recombinases are enzymes involved in genetic recombination and sometimes are involved in nucleic acid repair (e.g., recombinational DNA repair). Recombinases can initiate strand exchange, for example. Recombinases may include, for example, Cre recombinase, Hin recombinase, Tre recombinase, FLP recombinase, RecA, RAD51, RadA, T4 uvsX. In some embodiments, nucleic acid targets may be amplified without exposure to a recombinase accessory protein, such as, for example, a recombinase loading factor (e.g., T4 uvsY).

In some embodiments, nucleic acid targets may be amplified without exposure to a nucleic acid binding protein (e.g., single-stranded binding protein or single-strand DNA-binding protein (SSB)). Single stranded binding proteins generally function to prevent premature annealing, protect the single-stranded DNA from being digested by nucleases, and/or remove secondary structure from DNA (e.g., destabilize helical duplexes) to allow enable action by other enzymes. In some embodiments, nucleic acid targets may be amplified without exposure to a single-strand DNA-binding protein, such as, for example, T4 gp32.

In some embodiments, nucleic acid targets may be amplified without exposure to a topoisomerase. Topoisomerases are enzymes that regulate the overwinding or underwinding of DNA by binding to either single-stranded or double-stranded DNA and cutting the DNA phosphate backbone. Amplification conditions that do not include use of a topoisomerase may be referred to herein as topoisomerase-free amplification conditions.

Nucleic acid targets may be amplified with or without exposure to agents or conditions that destabilize nucleic acid. Destabilization generally refers to a disruption in the overall organization and geometric orientation of a nucleic acid molecule (e.g., double helical structure) by one or more of tilt, roll, twist, slip, and flip effects (e.g., as described in Lenglet et al., (2010) Journal of Nucleic Acids Volume 2010, Article ID 290935, 17 pages). Destabilization generally does not refer to melting or separation of nucleic acid strands, as described above for denaturation. Nucleic acid destabilization may be achieved, for example, by exposure to agents such as intercalators or alkylating agents, and/or chemicals such as formamide, urea, dimethyl sulfoxide (DMSO), or N,N,N-trimethylglycine (betaine). In some embodiments, amplification methods may include use of one or more destabilizing agents. In some embodiments, amplification methods exclude use of destabilizing agents.

In some embodiments, nucleic acid targets may be amplified without exposure to a ligase. Ligases are enzyme that can catalyze the joining of amino acid molecules by forming a new chemical bond. Amplification conditions that do not include use of a ligase may be referred to herein as ligase-free amplification conditions.

In some embodiments, nucleic acid targets may be amplified without exposure to an RNA replicase. RNA replicases, RNA-dependent RNA polymerase (RdRp), or RDR, are enzymes that catalyze the replication of RNA from an RNA template. Amplification conditions that do not include use of an RNA replicase may be referred to herein as RNA replicase-free amplification conditions.

Nucleic acid targets may be amplified without cleavage or digestion, in certain embodiments. For example, in some embodiments, nucleic acid is amplified without prior exposure to one or more cleavage agents, and intact nucleic acid is amplified. In certain embodiments, nucleic acid is amplified without exposure to one or more cleavage agents during amplification. In certain embodiments, nucleic acid is amplified without exposure to one or more cleavage agents after amplification. Amplification conditions that do not include use of a cleavage agent may be referred to herein as cleavage agent-free amplification conditions. The term "cleavage agent" generally refers to an agent, sometimes a chemical or an enzyme that can cleave a nucleic acid at one or more specific or non-specific sites. Specific cleavage agents often cleave specifically according to a particular nucleotide sequence at a particular site. Cleavage agents may include endonucleases (e.g., restriction enzymes, nicking enzymes, and the like); exonucleases (DNAses, RNAses (e.g., RNAseH), 5' to 3' exonucleases (e.g. exonuclease II), 3' to 5' exonucleases (e.g. exonuclease I), and poly(A)-specific 3' to 5' exonucleases); and chemical cleaving agents.

Nucleic acid targets may be amplified without use of restriction enzymes and/or nicking enzymes, in certain embodiments. A restriction enzyme is a protein that cuts DNA at a specific site and generally cleaves both strands of a double-stranded duplex, and a nicking enzyme is a protein that binds to double-stranded DNA and cleaves one strand of a double-stranded duplex. In certain embodiments, nucleic acid is amplified without prior exposure to restriction enzymes and/or nicking enzymes. In certain embodiments, nucleic acid is amplified without exposure to restriction enzymes and/or nicking enzymes during amplification. In certain embodiments, nucleic acid is amplified without exposure to restriction enzymes and/or nicking enzymes after amplification. Amplification conditions that do not include use of a restriction enzyme may be referred to herein as restriction enzyme-free amplification conditions. Amplification conditions that do not include use of a nicking enzyme may be referred to herein as nicking enzyme-free amplification conditions.

Nucleic acid targets may be amplified without exonuclease treatment, in certain embodiments. Exonucleases are enzymes that work by cleaving nucleotides one at a time from the end of a polynucleotide chain through a hydrolyzing reaction that breaks phosphodiester bonds at either the 3' or the 5' end. Exonucleases include, for example, DNAses, RNAses (e.g., RNAseH), 5' to 3' exonucleases (e.g. exonuclease II), 3' to 5' exonucleases (e.g. exonuclease I), and poly(A)-specific 3' to 5' exonucleases. In certain embodiments, nucleic acid is amplified without exonuclease treatment prior to amplification. In certain embodiments, nucleic acid is amplified without exonuclease treatment during amplification. In certain embodiments, nucleic acid is amplified without exonuclease after amplification. Amplification conditions that do not include use of an exonuclease may be referred to herein as exonuclease-free amplification conditions. In certain embodiments, nucleic acid is amplified without DNAse treatment. In certain embodiments, nucleic acid is amplified without RNAse treatment. In certain embodiments, nucleic acid is amplified without RNAseH treatment. Amplification conditions that do not include use of DNAse may be referred to herein as DNAse-free amplification conditions. Amplification conditions that do not include use of RNAse may be referred to herein as RNAse-free amplification conditions. Amplification conditions that do not include use of RNAseH may be referred to herein as RNAseH-free amplification conditions.

An amplified nucleic acid may be referred to herein as a nucleic acid amplification product or amplicon. In some embodiments, an amplification product may include naturally occurring nucleotides, non-naturally occurring nucleotides, nucleotide analogs and the like and combinations of the foregoing. An amplification product typically has a nucleotide sequence that is identical to or substantially identical to a sequence in a sample nucleic acid (e.g., target sequence) or complement thereof. A "substantially identical" nucleotide sequence in an amplification product will generally have a high degree of sequence identity to the nucleotide sequence being amplified or complement thereof (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% sequence identity), and variations sometimes are a result of polymerase infidelity or other variables.

In some embodiments, a nucleic acid amplification product comprises a polynucleotide that is continuously complementary to or substantially identical to a target sequence in sample nucleic acid. Continuously complementary generally refers to a nucleotide sequence in a first strand, for example, where each base in order (e.g., read 5' to 3') pairs with a correspondingly ordered base in a second strand, and there are no gaps, additional sequences or unpaired bases within the sequence considered as continuously complementary. Stated another way, continuously complementary generally refers to all contiguous bases of a nucleotide sequence in a first stand being complementary to corresponding contiguous bases of a nucleotide sequence in a second strand. For example, a first strand having a sequence 5'-ATGCATG-CATGC-3' (SEQ ID NO:10) would be considered as continuously complementary to a second strand having a sequence 5'-GCATGCATGCAT-3' (SEQ ID NO:11), where all contiguous bases in the first strand are complementary to all corresponding contiguous bases in the second strand. However, a first strand having a sequence 5'-ATGCAT-AAAAAAGCATGC-3' (SEQ ID NO:12) would not be considered as continuously complementary to a second strand having a sequence 5'-GCATGCATGCAT-3' (SEQ ID NO:11), because the sequence of six adenines (6 As) in the middle of the first strand would not pair with bases in the second strand. A continuously complementary sequence sometimes is about 5 contiguous bases to about 25 contiguous bases in length, sometimes is about 6 contiguous bases to about 20 contiguous bases in length, sometimes is about 7 contiguous bases to about 18 contiguous bases in length, and sometimes is about 8 contiguous bases to about 16 contiguous bases in length. In some embodiments, a nucleic acid amplification product consists of a polynucleotide that is continuously complementary to or substantially identical to a target sequence in sample nucleic acid. Accordingly, in some embodiments, a nucleic acid amplification product does not include any additional sequences (e.g., at the 5' and/or 3' end, or within the product) that are not continuously complementary to or substantially identical to a target sequence, such as, for example, additional sequences incorporated into an amplification product by way of tailed primers or ligation, and/or additional sequences providing cleavage agent recognition sites (e.g., nicking enzyme recognition sites). Generally, unless a target sequence comprises tandem repeats, an amplification product does not include product in the form of tandem repeats.

Nucleic acid amplification products may comprise sequences complementary to or substantially identical to one or more primers used in an amplification reaction. In some embodiments, a nucleic acid amplification product comprises a first nucleotide sequence that is continuously complementary to or identical to a first primer sequence, and a second nucleotide sequence that is continuously complementary to or identical to a second primer sequence.

In some embodiments, nucleic acid amplification products comprise a spacer sequence. Generally, a spacer sequence in an amplification product is a sequence (1 or more bases) continuously complementary to or substantially identical to a portion of a target sequence in the sample nucleic acid, and is flanked by sequences in the amplification product that are complementary to or substantially identical to one or more primers used in an amplification reaction. A spacer sequence flanked by sequences in the amplification product generally lies between a first sequence (complementary to or substantially identical to a first primer) and a second sequence (complementary to or substantially identical to a second primer). Thus, an amplification product typically includes a first sequence followed by a spacer sequences followed by a second sequence. A spacer sequence generally is not complementary to or substantially identical to a sequence in the primer(s). In some embodiments, a spacer sequence comprises about 1 to 10 bases. For example, a spacer sequence may comprise 1 base, 2 bases, 3 bases, 4 bases, 5 bases, 6 bases, 7 bases, 8 bases, 9 bases, or 10 bases. In some embodiments, a spacer sequence comprises about 1 to 5 bases.

In some embodiments, a nucleic acid amplification product consists of a first nucleotide sequence that is continuously complementary to or identical to a first primer sequence, a second nucleotide sequence that is continuously complementary to or identical to a second primer sequence, and a spacer sequence. Accordingly, in some embodiments, a nucleic acid amplification product does not include any additional sequences (e.g., at the 5' and/or 3' end; or within the product) that are not continuously complementary to or identical to a first primer sequence and a second primer sequence, and are not part of a spacer sequence, such as, for example, additional sequences incorporated into an amplification product by way of tailed or looped primers, ligation or other mechanism.

In some embodiments, a nucleic acid amplification product consists essentially of a first nucleotide sequence that is continuously complementary to or identical to a first primer sequence, a second nucleotide sequence that is continuously complementary to or identical to a second primer sequence, and a spacer sequence. Accordingly, in some embodiments, a nucleic acid amplification product generally does not include additional sequences (e.g., at the 5' and/or 3' end; or within the product) that are not continuously complementary to or identical to a first primer sequence and a second primer sequence, and are not part of a spacer sequence, such as, for example, additional sequences incorporated into an amplification product by way of tailed or looped primers, ligation or other mechanism. However, in such embodiments, a nucleic acid amplification product may include, for example, some mismatched (i.e., non-complementary) bases or one more extra bases (e.g., at the 5' and/or 3' end; or within the product) introduced into the product by way of error or promiscuity in the amplification process.

Nucleic acid amplification products may be up to 50 bases in length. In some embodiments, a nucleic acid amplification product is about 15 to about 40 bases long. For example, a nucleic acid amplification product may be 15 bases long, 16 bases long, 17 bases long, 18 bases long, 19 bases long, 20 bases long, 21 bases long, 22 bases long, 23 bases long, 24 bases long, 25 bases long, 26 bases long, 27 bases long, 28 bases long, 29 bases long, 30 bases long, 31 bases long, 32 bases long, 33 bases long, 34 bases long, 35 bases long, 36 bases long, 37 bases long, 38 bases long, 39 bases long, or 40 bases long. In some embodiments, an amplification product is about 20 to about 40 bases long. In some embodiments, an amplification product is about 20 to about 30 bases long. In some embodiments, nucleic acid amplification products for a given target sequence have the same length or substantially the same length (e.g., within 1 to 5 bases). Accordingly, nucleic acid amplification products for a given target sequence may produce a single signal (e.g., band on an electrophoresis gel) and generally do not produce multiple signals indicative of multiple lengths (e.g., a ladder or smear on an electrophoresis gel). For multiplex reactions, nucleic acid amplification products for different target sequences may have different lengths.

The methods and components described herein may be used for multiplex amplification. Multiplex amplification generally refers to the amplification of more than one nucleic acid of interest (e.g., amplification or more than one target sequence). For example, multiplex amplification can refer to amplification of multiple sequences from the same sample or amplification of one of several sequences in a sample. Multiplex amplification also may refer to amplification of one or more sequences present in multiple samples either simultaneously or in step-wise fashion. For example, a multiplex amplification may be used for amplifying least two target sequences that are capable of being amplified (e.g., the amplification reaction comprises the appropriate primers and enzymes to amplify at least two target sequences). In some instances, an amplification reaction may be prepared to detect at least two target sequences, but only one of the target sequences may be present in the sample being tested, such that both sequences are capable of being amplified, but only one sequence is amplified. In some instances, where two target sequences are present, an amplification reaction may result in the amplification of both target sequences. A multiplex amplification reaction may result in the amplification of one, some, or all of the target sequences for which it comprises the appropriate primers and enzymes. In some instances, an amplification reaction may be prepared to detect two sequences with one pair of primers, where one sequence is a target sequence and one sequence is a control sequence (e.g., a synthetic sequence capable of being amplified by the same primers as the target sequence and having a different spacer base or sequence than the target). In some instances, an amplification reaction may be prepared to detect multiple sets of sequences with corresponding primer pairs, where each set includes a target sequence and a control sequence.

Primers

Nucleic acid amplification generally is conducted in the presence of one or more primers. A primer is generally characterized as an oligonucleotide that includes a nucleotide sequence capable of hybridizing or annealing to a target nucleic acid, at or near (e.g., adjacent to) a specific region of interest (i.e., target sequence). Primers can allow for specific determination of a target nucleic acid nucleotide sequence or detection of the target nucleic acid (e.g., presence or absence of a sequence), or feature thereof, for example. A primer may be naturally occurring or synthetic. The term specific, or specificity, generally refers to the binding or hybridization of one molecule to another molecule, such as a primer for a target polynucleotide. That is, specific or specificity refers to the recognition, contact, and formation of a stable complex between two molecules, as compared to substantially less recognition, contact, or complex formation of either of those two molecules with other molecules. The term anneal or hybridize generally refers to the formation of a stable complex between two molecules. The terms primer, oligo, or oligonucleotide may be used interchangeably herein, when referring to primers.

A primer may be designed and synthesized using suitable processes, and may be of any length suitable for hybridizing to a target sequence and performing an amplification process described herein. Primers often are designed according to a sequence in a target nucleic acid. A primer in some embodiments may be about 5 bases in length to about 30 bases in length. For example, a primer may be 5, 6, 7, 8, 9, 10, 11, 12, 13, 14, 15, 16, 17, 18, 19, 20, 21, 22, 23, 24, 25, 26, 27, 28, 29 or 30 bases in length. In some embodiments, a primer is less than 28 bases in length. In some embodiments, a primer is about 8 to about 16 bases in length. In some embodiments, a primer is about 10 to about 12 bases in length. A primer may be composed of naturally occurring and/or non-naturally occurring nucleotides (e.g., modified nucleotides, labeled nucleotides), or a mixture thereof. Primers suitable for use with methods described herein may be synthesized and labeled using any suitable technique. For example, primers may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of primers may be effected, for example, by native acrylamide gel electrophoresis or by anion-exchange high-performance liquid chromatography (HPLC), for example, as described in Pearson and Regnier, J. Chrom., 255:137-149, 1983.

In some embodiments, a primer comprises modified nucleotides. In some embodiments, a primer consists essentially of modified nucleotides. In some embodiments, a primer consists of modified nucleotides. A nucleotide (or base) may be modified according to any modification described herein or known in the art. Modifications may include those made during primer synthesis and/or may include post-synthetic modifications. Modifications may include internal modifications, modifications and the 3' end of a primer, and/or modifications at the 5' end of a primer. In some embodiments, a primer comprises a mixture of modified and unmodified nucleotides. In some embodiments, a primer comprises unmodified nucleotides. In some embodiments, a primer consists essentially of unmodified nucleotides. In some embodiments, a primer consists of unmodified nucleotides.

Modifications and modified bases may include, for example, phosphorylation, (e.g., 3' phosphorylation, 5' phosphorylation); attachment chemistry or linkers modifications (e.g., Acrydite™, adenylation, azide (NHS ester), digoxigenin (NHS ester), cholesteryl-TEG, I-Linker™, amino modifiers (e.g., amino modifier C6, amino modifier C12, amino modifier C6 dT, Uni-Link™ amino modifier), alkynes (e.g., 5' hexynyl, 5-octadiynyl dU), biotinylation (e.g., biotin, biotin (azide), biotin dT, biotin-TEG, dual biotin, PC biotin, desthiobiotin-TEG), thiol modifications (e.g., thiol modifier C3 S-S, dithiol, thiol modifier C6 S-S)); fluorophores (e.g., Freedom™ Dyes, Alexa Fluor® Dyes, LI-COR IRDyes®, ATTO™ Dyes, Rhodamine Dyes, WellRED Dyes, 6-FAM (azide), Texas Red®-X (NHS ester), Lightcycler® 640 (NHS ester), Dy 750 (NHS ester)); Iowa Black® dark quenchers modifications (e.g., Iowa Black®

FQ, Iowa Black® RQ); dark quenchers modifications (e.g., Black Hole Quencher®-1, Black Hole Quencher®-2, Dabcyl); spacers (C3 spacer, PC spacer, hexanediol, spacer 9, spacer 18, 1',2'-dideoxyribose (dSpacer); modified bases (e.g., 2-aminopurine, 2,6-diaminopurine (2-amino-dA), 5-bromo dU, deoxyUridine, inverted dT, inverted dideoxy-T, dideoxy-C, 5-methyl dC, deoxyInosine, Super T®, Super G®, locked nucleic acids (LNA's), 5-nitroindole, 2'-O-methyl RNA bases, hydroxmethyl dC, UNA unlocked nucleic acid (e.g., UNA-A, UNA-U, UNA-C, UNA-G), Iso-dC, Iso-dG, Fluoro C, Fluoro U, Fluoro A, Fluoro G); phosphorothioate bonds modifications (e.g., phosphorothioated DNA bases, phosphorothioated RNA bases, phosphorothioated 2' O-methyl bases, phosphorothioated LNA bases); and click chemistry modifications. In some embodiments, modifications and modified bases include uracil bases, ribonucleotide bases, O-methyl RNA bases, phosphorothioate linkages, 3' phosphate groups, spacer bases (such as C3 spacer or other spacer bases). For example, a primer may comprise one or more O-methyl RNA bases (e.g., 2'-O-methyl RNA bases). 2'-O-methyl RNA generally is a post-transcriptional modification of RNA found in tRNA and other small RNAs. Primers can be directly synthesized that include 2'-O-methyl RNA bases. This modification can, for example, increase Tm of RNA:RNA duplexes and provide stability in the presence of single-stranded ribonucleases and DNases. 2'-O-methyl RNA bases may be included in primers, for example, to increase stability and binding affinity to a target sequence. In some embodiments, a primer may comprise one or more phosphorothioate linkages (e.g., phosphorothioate bond modifications). A phosphorothioate (PS) bond substitutes a sulfur atom for a non-bridging oxygen in the phosphate backbone of a primer. This modification typically renders the internucleotide linkage resistant to nuclease degradation. Phosphorothioate bonds may be introduced between about the last 3 to 5 nucleotides at the 5'-end or the 3'-end of a primer to inhibit exonuclease degradation, for example. Phosphorothioate bonds included throughout an entire primer can help reduce attack by endonucleases, in certain instances. In some embodiments, a primer may comprise a 3' phosphate group. 3' phosphorylation can inhibit degradation by certain 3'-exonucleases and can be used to block extension by DNA polymerases, in certain instances. In some embodiments, a primer may comprise one or more spacer bases (e.g., one or more C3 spacers). A C3 spacer phosphoramidite can be incorporated internally or at the 5'-end of a primer. Multiple C3 spacers may be added at either end of a primer to introduce a long hydrophilic spacer arm for the attachment of fluorophores or other pendent groups, for example.

In some embodiments, a primer comprises DNA bases. In some embodiments, a primer comprises RNA bases. In some embodiments, a primer comprises a mixture of DNA bases and RNA bases. DNA bases may be modified or unmodified. RNA bases may be modified or unmodified. In some embodiments, a primer consists essentially of DNA bases (e.g., modified DNA bases and/or unmodified DNA bases). In some embodiments, a primer consists of DNA bases (e.g., modified DNA bases and/or unmodified DNA bases). In some embodiments, a primer consists essentially of unmodified DNA bases. In some embodiments, a primer consists of unmodified DNA bases. In some embodiments, a primer consists essentially of modified DNA bases. In some embodiments, a primer consists of modified DNA bases. In some embodiments, a primer consists essentially of RNA bases (e.g., modified RNA bases and/or unmodified RNA bases). In some embodiments, a primer consists of RNA bases (e.g., modified RNA bases and/or unmodified RNA bases). In some embodiments, a primer consists essentially of unmodified RNA bases. In some embodiments, a primer consists of unmodified RNA bases. In some embodiments, a primer consists essentially of modified RNA bases. In some embodiments, a primer consists of modified RNA bases.

In some embodiments, a primer comprises no RNA bases. In some embodiments, a primer comprises no RNA bases at the 3' end. In some embodiments, a primer comprises a DNA base (or modified DNA base) at the 3' end. In some embodiments, a primer is not a chimeric primer. A chimeric primer is a primer comprising DNA and RNA bases. In some embodiments, a primer is a homogeneous primer. In some embodiments, a primer is a homogeneous DNA primer. A homogeneous DNA primer may comprise unmodified DNA bases, modified DNA bases, or a mixture of modified DNA bases and unmodified DNA bases, and generally do not include RNA bases.

In some embodiments, a primer comprises no cleavage agent recognition sites. For example, a primer herein may comprise no nicking enzyme recognition sites. In some embodiments, a primer comprises no tail. In some embodiments, a primer comprises no tail comprising a nicking enzyme recognition site.

All or a portion of a primer sequence may be complementary or substantially complementary to a target nucleic acid, in some embodiments. Substantially complementary with respect to sequences generally refers to nucleotide sequences that will hybridize with each other. The stringency of the hybridization conditions can be altered to tolerate varying amounts of sequence mismatch. In some embodiments, target and primer sequences are at least 75% complementary to each other. For example, target and primer sequences may be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other.

Primers that are substantially complimentary to a target nucleic acid sequence typically are also substantially identical to the compliment of the target nucleic acid sequence. That is, primers are substantially identical to the anti-sense strand of the nucleic acid. Substantially identical with respect to sequences generally refers to nucleotide sequences that are at least 75% identical to each other. For example, primers that are substantially identical to the anti-sense strand of a target nucleic acid may 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

In some embodiments, primers comprise a pair of primers. A pair of primers may include a forward primer and a reverse primer (e.g., primers that bind to the sense and antisense strands of a target nucleic acid). In some embodiments, primers consist of a pair of primers (i.e. a forward primer and a reverse primer). Accordingly, in some embodiments, amplification of a target sequence is performed using a pair of primers and no additional primers or oligonucleotides are included in the amplification of the target sequence (e.g., the amplification reaction components comprise no additional primer pairs for a given target sequence, no nested primers, no bumper primers, no oligonucleotides other than the primers, no probes, and the like). In some embodiments, primers consist of a pair of primers, however, in certain instances, an amplification reaction may include additional primer pairs for amplifying different target sequences, such as in a multiplex amplification. In some embodiments, primers consist of a pair of primers, however, in certain instances, an amplification reaction may include additional primers, oligonucleotides or probes for a detection process that are not considered part of amplification.

In some embodiments primers are used in sets. An amplification primer set may include a pair of forward and reverse primers for a given target sequence. For multiplex amplification, primers that amplify a first target sequence are considered a primer set, and primers that amplify a second target sequence are considered a different primer set.

In some embodiments, amplification reaction components comprise a first primer (first oligonucleotide) complementary to a target sequence in a first strand (e.g., sense strand, forward strand) of a sample nucleic acid, and a second primer (second oligonucleotide) complementary to a target sequence in a second strand (e.g., antisense strand, reverse strand) of a sample nucleic acid. In some embodiments, a first primer (first oligonucleotide) comprises a first polynucleotide continuously complementary to a target sequence in a first strand of sample nucleic acid, and a second primer (second oligonucleotide) comprises a second polynucleotide continuously complementary to a target sequence in a second strand of sample nucleic acid. Continuously complementary for a primer-target generally refers to a nucleotide sequence in a primer, where each base in order pairs with a correspondingly ordered base in a target sequence, and there are no gaps, additional sequences or unpaired bases within the sequence considered as continuously complementary. Stated another way, continuously complementary generally refers to all contiguous bases of a nucleotide sequence in a primer being complementary to corresponding contiguous bases of a nucleotide sequence in a target.

In some embodiments, a first primer (first oligonucleotide) consists of a first polynucleotide continuously complementary to a target sequence in a first strand of sample nucleic acid, and a second primer (second oligonucleotide) consists of a second polynucleotide continuously complementary to a target sequence in the second strand of the sample nucleic acid. Accordingly, in some embodiments, a primer does not include any additional sequences (e.g., at the 5' and/or 3' end, or within the primer) that are not continuously complementary to a target sequence, such as, for example, additional sequences present in tailed primers or looped primers, and/or additional sequences providing cleavage agent recognition sites (e.g., nicking enzyme recognition sites). In some embodiments, amplification reaction components do not comprise primers comprising additional sequences (i.e., sequences other than the sequence that is continuously complementary to a target sequence) such as, for example, tailed primers, looped primers, primers capable of forming step-loop structures, hairpin structures, and/or additional sequences providing cleavage agent recognition sites (e.g., nicking enzyme recognition sites), and the like.

In some embodiments, a first primer (first oligonucleotide) consists essentially of a first polynucleotide continuously complementary to a target sequence in a first strand of sample nucleic acid, and a second primer (second oligonucleotide) consists essentially of a second polynucleotide continuously complementary to a target sequence in the second strand of the sample nucleic acid. Accordingly, in some embodiments, a primer generally does not include any additional sequences (e.g., at the 5' and/or 3' end, or within the primer) that are not continuously complementary to a target sequence, such as, for example, additional sequences present in tailed primers or looped primers, and/or additional sequences providing cleavage agent recognition sites (e.g., nicking enzyme recognition sites). However, in such embodiments, a primer may include one or more additional bases (e.g., at the 5' and/or 3' end, or within the primer) that do not add a functional feature to the primer. For example, additional sequences present in tailed primers or looped primers generally add a functional feature and would be excluded from primers in such embodiments.

A primer, in certain embodiments, may contain a modification such as one or more inosines, abasic sites, locked nucleic acids, minor groove binders, duplex stabilizers (e.g., acridine, spermidine), Tm modifiers or any modifier that changes the binding properties of the primer. A primer, in certain embodiments, may contain a detectable molecule or entity (e.g., a fluorophore, radioisotope, colorimetric agent, particle, enzyme and the like).

Polymerase

In some embodiments, amplification reaction components comprise one or more polymerases. Polymerases are proteins capable of catalyzing the specific incorporation of nucleotides to extend a 3' hydroxyl terminus of a primer molecule, such as, for example, an amplification primer described herein, against a nucleic acid target sequence (e.g., to which a primer is annealed). Polymerases may include, for example, thermophilic or hyperthermophilic polymerases that can have activity at an elevated reaction temperature (e.g., above 55 degrees Celsius, above 60 degrees Celsius, above 65 degrees Celsius, above 70 degrees Celsius, above 75 degrees Celsius, above 80 degrees Celsius, above 85 degrees Celsius, above 90 degrees Celsius, above 95 degrees Celsius, above 100 degrees Celsius). A hyperthermophilic polymerase may be referred to as a hyperthermophile polymerase. A polymerase having hyperthermophilic polymerase activity may be referred to as having hyperthermophile polymerase activity. A polymerase may or may not have strand displacement capabilities. In some embodiments, a polymerase can incorporate about 1 to about 50 nucleotides in a single synthesis. For example, a polymerase may incorporate about 5, 10, 15, 20, 25, 30, 35, 40, 45 or 50 nucleotides in a single synthesis. In some embodiments, a polymerase, can incorporate 20 to 40 nucleotides in a single synthesis. In some embodiments, a polymerase, can incorporate up to 50 nucleotides in a single synthesis. In some embodiments, a polymerase, can incorporate up to 40 nucleotides in a single synthesis. In some embodiments, a polymerase, can incorporate up to 30 nucleotides in a single synthesis. In some embodiments, a polymerase, can incorporate up to 20 nucleotides in a single synthesis.

In some embodiments, amplification reaction components comprise one or more DNA polymerases. In some embodiments, amplification reaction components comprise one or more DNA polymerases selected from the following: 9°N DNA polymerase; 9°Nm™ DNA polymerase; Therminator™ DNA Polymerase; Therminator™ II DNA Polymerase; Therminator™ III DNA Polymerase; Therminator™ γ DNA Polymerase; Bst DNA polymerase; Bst DNA polymerase (large fragment); Phi29 DNA polymerase, DNA polymerase I (*E. coli*), DNA polymerase I, large (Klenow) fragment; Klenow fragment (3'-5' exo-); T4 DNA polymerase; T7 DNA polymerase; Deep VentR™ (exo-) DNA Polymerase; Deep VentR™ DNA Polymerase; DyNAzyme™ EXT DNA; DyNAzyme™ II Hot Start DNA Polymerase; Phusion™ High-Fidelity DNA Polymerase; VentR® DNA Polymerase; VentR® (exo-) DNA Polymerase; RepliPHI™ Phi29 DNA Polymerase; rBst DNA Polymerase, large fragment (IsoTherm™ DNA Polymerase); MasterAmp™ AmpliTherm™ DNA Polymerase; Taq DNA polymerase; Tth DNA polymerase; Tfl DNA polymerase; Tgo DNA polymerase; SP6 DNA polymerase; Tbr DNA polymerase; DNA polymerase Beta; and ThermoPhi DNA polymerase.

In some embodiments, amplification reaction components comprise one or more hyperthermophile DNA polymerases. Generally, hyperthermophile DNA polymerases are thermostable at high temperatures. For example, a hyperthermophile DNA polymerase may have a half-life of about 5 to 10 hours at 95 degrees Celsius and a half-life of about 1 to 3 hours at 100 degrees Celsius. In some embodiments, amplification reaction components comprise one or more hyperthermophile DNA polymerases from Archaea. In some embodiments, amplification reaction components comprise one or more hyperthermophile DNA polymerases from Thermococcus. In some embodiments, amplification reaction components comprise one or more hyperthermophile DNA polymerases from Thermococcaceaen archaean. In some embodiments, amplification reaction components comprise one or more hyperthermophile DNA polymerases from Pyrococcus. In some embodiments, amplification reaction components comprise one or more hyperthermophile DNA polymerases from Methanococcaceae. In some embodiments, amplification reaction components comprise one or more hyperthermophile DNA polymerases from Methanococcus. In some embodiments, amplification reaction components comprise one or more hyperthermophile DNA polymerases from Thermus. In some embodiments, amplification reaction components comprise one or more hyperthermophile DNA polymerases from Thermus thermophiles.

In some embodiments, amplification reaction components comprise a hyperthermophile DNA polymerase or functional fragment thereof. A functional fragment generally retains one or more functions of a full-length polymerase such as, for example, the capability to polymerize DNA (e.g., in an amplification reaction). In some instances, a functional fragment performs a function (e.g., polymerization of DNA in an amplification reaction) at a level that is at least about 50% the level of function for a full length polymerase. In some instances, a functional fragment performs a function (e.g., polymerization of DNA in an amplification reaction) at a level that is at least about 75% the level of function for a full length polymerase. In some instances, a functional fragment performs a function (e.g., polymerization of DNA in an amplification reaction) at a level that is at least about 90% the level of function for a full length polymerase. In some instances, a functional fragment performs a function (e.g., polymerization of DNA in an amplification reaction) at a level that is at least about 95% the level of function for a full length polymerase. Levels of polymerase activity can be assessed, for example, using a detectable nucleic acid amplification method, such as, for example, a detectable nucleic acid amplification method described herein. In some embodiments, amplification reaction components comprise a hyperthermophile DNA polymerase comprising an amino acid sequence of SEQ ID NO:8 or a functional fragment of SEQ ID NO:8. In some embodiments, amplification reaction components comprise a hyperthermophile DNA polymerase comprising an amino acid sequence of SEQ ID NO:9 or a functional fragment of SEQ ID NO:9.

In some embodiments, amplification reaction components comprise a polymerase comprising an amino acid sequence that is at least about 90% identical to a hyperthermophile polymerase or a functional fragment thereof (i.e., a functional fragment as described herein of a polymerase comprising an amino acid sequence that is at least about 90% identical to a hyperthermophile polymerase). The degree of sequence identity can be determined, for example, by performing an amino acid sequence alignment. In some embodiments, amplification reaction components comprise a polymerase comprising an amino acid sequence that is at least about 90% identical to the amino acid sequence of SEQ ID NO:8 or a functional fragment thereof (i.e., a functional fragment as described herein of a polymerase comprising an amino acid sequence that is at least about 90% identical to SEQ ID NO:8). In some embodiments, amplification reaction components comprise a polymerase comprising an amino acid sequence that is at least about 95% identical to the amino acid sequence of SEQ ID NO:8 or a functional fragment thereof. In some embodiments, amplification reaction components comprise a polymerase comprising an amino acid sequence that is at least about 99% identical to the amino acid sequence of SEQ ID NO:8 or a functional fragment thereof. In some embodiments, amplification reaction components comprise a polymerase comprising an amino acid sequence that is at least about 90% identical to the amino acid sequence of SEQ ID NO:9 or a functional fragment thereof (i.e., a functional fragment as described herein of a polymerase comprising an amino acid sequence that is at least about 90% identical to SEQ ID NO:9). In some embodiments, amplification reaction components comprise a polymerase comprising an amino acid sequence that is at least about 95% identical to the amino acid sequence of SEQ ID NO:9 or a functional fragment thereof. In some embodiments, amplification reaction components comprise a polymerase comprising an amino acid sequence that is at least about 99% identical to the amino acid sequence of SEQ ID NO:9 or a functional fragment thereof.

In some embodiments, a polymerase may possess reverse transcription capabilities. In such instances, an amplification reaction can amplify RNA targets, for example, in a single step without the use of a separate reverse transcriptase. Non-limiting examples of polymerases that possess reverse transcriptase capabilities include Bst (large fragment), 9°N DNA polymerase, 9°Nm™ DNA polymerase, Therminator™, Therminator™ II, and the like). In some embodiments, amplification reaction components comprise one or more separate reverse transcriptases. In some embodiments, more than one polymerase may be included in in an amplification reaction. For example, an amplification reaction may comprise a polymerase having reverse transcriptase activity and a second polymerase having no reverse transcriptase activity.

In some embodiments, one or more polymerases having exonuclease activity are used during amplification. In some embodiments, one or more polymerases having no exonuclease activity are used during amplification. In some embodiments, one or more polymerases having low exonuclease activity are used during amplification. In certain instances, a polymerase having no or low exonuclease activity comprises one or more modifications (e.g., amino acid substitutions) that reduce or eliminate the exonuclease activity of the polymerase. A modified polymerase having low exonuclease activity may have 10% or less exonuclease activity compared to an unmodified polymerase. For example, a modified polymerase having low exonuclease activity may have less than about 10%, 9%, 8%, 7%, 6%, 5%, 4%, 3%, 2%, or 1% exonuclease activity compared to an unmodified polymerase. In some embodiments, a polymerase has no or low 5' to 3' exonuclease activity. In some embodiments, a polymerase has no or low 3' to 5' exonuclease activity. In some embodiments, a polymerase has no or low single strand dependent exonuclease activity. In some embodiments, a polymerase has no or low double strand dependent exonuclease activity. Non limiting examples of certain modifications that can reduce or eliminate exonuclease activity for a polymerase include one or more amino acid substitutions at position 141 and/or 143 and/or 458 of SEQ ID NO:8, or at a position corresponding to position 141 and/or 143 and/or 458 of SEQ ID NO:8. An amino acid position corresponding to a position in SEQ ID NO:8 may be identified, for example, by performing an amino acid sequence alignment. In some instances, modification(s) include a substitution of the native amino acid at position 141 to an alanine. In some instances the modification(s) include D141A. In some instances, modification(s) include a substitution of the native amino acid at position 143 to an alanine. In some instances the modification(s) include E143A. In some instances, modification(s) include a substitution of the native amino acid at position 143 to an aspartate. In some instances the modification(s) include E143D. In some instances, modification(s) include a substitution of the native amino acid at position 485 to a leucine. In some instances the modification(s) include A485L. In some instances, the modifications include D141A, E143A and A485L.

Detection and Quantification

The methods described herein may further comprise detecting and/or quantifying a nucleic acid amplification product. An amplification product may be detected and/or quantified by any suitable detection and/or quantification method including, for example, any detection method or quantification method described herein. Non-limiting examples of detection and/or quantification methods include molecular beacon (e.g., real-time, endpoint), lateral flow, fluorescence resonance energy transfer (FRET), fluorescence polarization (FP), surface capture, 5' to 3' exonuclease hydrolysis probes (e.g., TAQMAN), intercalating/binding dyes, absorbance methods (e.g., colorimetric, turbidity), electrophoresis (e.g., gel electrophoresis, capillary electrophoresis), mass spectrometry, nucleic acid sequencing, digital amplification, a primer extension method (e.g., iPLEX™), Molecular Inversion Probe (MIP) technology from Affymetrix, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), colorimetric oligonucleotide ligation assay (OLA), sequence-coded OLA, microarray ligation, ligase chain reaction, padlock probes, invader assay, hybridization using at least one probe, hybridization using at least one fluorescently labeled probe, cloning and sequencing, the use of hybridization probes and quantitative real time polymerase chain reaction (QRT-PCR), nanopore sequencing, chips and combinations thereof. In some embodiments, detecting a nucleic acid amplification product comprises use of a real-time detection method (i.e., product is detected and/or continuously monitored during an amplification process). In some embodiments, detecting a nucleic acid amplification product comprises use of an endpoint detection method (i.e., product is detected after completing or stopping an amplification process). Nucleic acid detection methods may also employ the use of labeled nucleotides incorporated directly into a target sequence or into probes containing complementary sequences to a target. Such labels may be radioactive and/or fluorescent in nature and can be resolved in any of the manners discussed herein. In some embodiments, quantification of a nucleic acid amplification product may be achieved using certain detection methods described below. In certain instances, a detection method may be used in conjunction with a measurement of signal intensity, and/or generation of (or reference to) a standard curve and/or look-up table for quantification of a nucleic acid amplification product.

In some embodiments, detecting a nucleic acid amplification product comprises use of molecular beacon technology. The term molecular beacon generally refers to a detectable molecule, where the detectable property of the molecule is detectable under certain conditions, thereby enabling the molecule to function as a specific and informative signal. Non-limiting examples of detectable properties include, optical properties (e.g., fluorescence), electrical properties, magnetic properties, chemical properties and time or speed through an opening of known size. Molecular beacons for detecting nucleic acid molecules may be, for example, hair-pin shaped oligonucleotides containing a fluorophore on one end and a quenching dye on the opposite end. The loop of the hair-pin may contain a probe sequence that is complementary to a target sequence and the stem is formed by annealing of complementary arm sequences located on either side of the probe sequence. A fluorophore and a quenching molecule can be covalently linked at opposite ends of each arm. Under conditions that prevent the oligonucleotides from hybridizing to its complementary target or when the molecular beacon is free in solution, the fluorescent and quenching molecules are proximal to one another preventing fluorescence resonance energy transfer (FRET). When the molecular beacon encounters a target molecule (e.g., a nucleic acid amplification product), hybridization can occur, and the loop structure is converted to a stable more rigid conformation causing separation of the fluorophore and quencher molecules leading to fluorescence (Tyagi et al. Nature Biotechnology 14: March 1996, 303-308). Due to the specificity of the probe, the generation of fluorescence generally is exclusively due to the synthesis of the intended amplified product. In some instances, a molecular beacon probe sequence hybridizes to a sequence in an amplification product that is identical to or complementary to a sequence in a target nucleic acid. In some instances, a molecular beacon probe sequence hybridizes to a sequence in an amplification product that is not identical to or complementary to a sequence in a target nucleic acid (e.g., hybridizes to a sequence added to an amplification product by way of a tailed amplification primer or ligation).

Molecular beacons are highly specific and can discern a single nucleotide polymorphism. Molecular beacons also can be synthesized with different colored fluorophores and different target sequences, enabling simultaneous detection of several products in the same reaction (e.g., in a multiplex reaction). For quantitative amplification processes, molecular beacons can specifically bind to the amplified target following each cycle of amplification, and because non-hybridized molecular beacons are dark, it is not necessary to isolate the probe-target hybrids to quantitatively determine the amount of amplified product. The resulting signal is proportional to the amount of amplified product. Detection using molecular beacons can be done in real time or as an end-point detection method. In some instances, certain reaction conditions may be optimized for each primer/probe set to ensure accuracy and precision.

In some embodiments, detecting a nucleic acid amplification product comprises use of lateral flow. Use of lateral flow typically includes use of a lateral flow device. These devices generally include a solid phase fluid permeable flow path through which fluid flows through by capillary force. Example devices include, but are not limited to, dipstick assays and thin layer chromatographic plates with various appropriate coatings. Immobilized on the flow path are various binding reagents for the sample, binding partners or conjugates involving binding partners for the sample and signal producing systems. Detection can be achieved in several manners including, for example, enzymatic detection, nanoparticle detection, colorimetric detection, and fluorescence detection. Enzymatic detection may involve enzyme-labeled probes that are hybridized to complementary nucleic aid targets on the surface of the lateral flow device. The resulting complex can be treated with appropriate markers to develop a readable signal. Nanoparticle detection involves bead technology that may use colloidal gold, latex and/or paramagnetic nanoparticles. In one example, beads may be conjugated to an anti-biotin antibody. Target sequences may be directly biotinylated, or target sequences may be hybridized to sequence-specific biotinylated probes. Gold and latex give rise to colorimetric signals visible to the naked eye, and paramagnetic particles give rise to a non-visual signal when excited in a magnetic field and can be interpreted by a specialized reader. Fluorescence-based lateral flow detection methods also may be used and include, for example, dual fluorescein and biotin-labeled oligo probe methods, UPT-N ALP utilizing up-converting phosphor reporters composed of lanthanide elements embedded in a crystal (Corstjens et al., Clinical Chemistry, 47:10, 1885-1893, 2001), and the use of quantum dots.

Nucleic acids may be captured on lateral flow devices. Means of capture may include antibody-dependent and antibody-independent methods. Antibody-dependent capture generally comprises an antibody capture line and a labeled probe of complementary sequence to the target. Antibody-independent capture generally uses non-covalent interactions between two binding partners, for example, the high affinity and irreversible linkage between a biotinylated probe and a streptavidin line. Capture probes may be immobilized directly on lateral flow membranes. Both antibody-dependent and antibody-independent methods may be used, for example, for detecting amplification products generated in a multiplex reaction.

In some embodiments, detecting a nucleic acid amplification product comprises use of fluorescence resonance energy transfer (FRET). FRET is an energy transfer mechanism between two chromophores: a donor and an acceptor molecule. Briefly, a donor fluorophore molecule is excited at a specific excitation wavelength. The subsequent emission from the donor molecule as it returns to its ground state may transfer excitation energy to the acceptor molecule through a long range dipole-dipole interaction. The emission intensity of the acceptor molecule can be monitored and is a function of the distance between the donor and the acceptor, the overlap of the donor emission spectrum and the acceptor absorption spectrum and the orientation of the donor emission dipole moment and the acceptor absorption dipole moment. FRET can be useful for quantifying molecular dynamics, for example, in DNA-DNA interactions as described for molecular beacons. For monitoring the production of a specific product, a probe can be labeled with a donor molecule on one end and an acceptor molecule on the other. Probe-target hybridization brings a change in the distance or orientation of the donor and acceptor and FRET change is observed.

In some embodiments, detecting a nucleic acid amplification product comprises use of fluorescence polarization (FP). Fluorescence polarization techniques generally are based on the principle that a fluorescently labeled compound when excited by linearly polarized light will emit fluorescence having a degree of polarization inversely related to its rate of rotation. Therefore, when a molecule such as a tracer-nucleic acid conjugate, for example, having a fluorescent label is excited with linearly polarized light, the emitted light remains highly polarized because the fluorophore is constrained from rotating between the time light is absorbed and emitted. When a free tracer compound (i.e., unbound to a nucleic acid) is excited by linearly polarized light, its rotation is much faster than the corresponding tracer-nucleic acid conjugate and the molecules are more randomly oriented, therefore, the emitted light is depolarized. Thus, fluorescence polarization provides a quantitative means for measuring the amount of tracer-nucleic acid conjugate produced in an amplification reaction.

In some embodiments, detecting a nucleic acid amplification product comprises use of surface capture. This may be accomplished by the immobilization of specific oligonucleotides to a surface producing a biosensor that is both highly sensitive and selective. Example surfaces that may be used include gold and carbon, and a surface capture method may use a number of covalent or noncovalent coupling methods to attach a probe to the surface. The subsequent detection of a target nucleic acid can be monitored by a variety of methods.

In some embodiments, detecting a nucleic acid amplification product comprises use of 5' to 3' exonuclease hydrolysis probes (e.g., TAQMAN). TAQMAN probes, for example, are hydrolysis probes that can increase the specificity of a quantitative amplification method (e.g., quantitative PCR). The TAQMAN probe principle relies on 1) the 5' to 3' exonuclease activity of Taq polymerase to cleave a dual-labeled probe during hybridization to a complementary target sequence and 2) fluorophore-based detection. A resulting fluorescence signal permits quantitative measurements of the accumulation of amplification product during the exponential stages of amplification, and the TAQMAN probe can significantly increase the specificity of the detection.

In some embodiments, detecting a nucleic acid amplification product comprises use of intercalating and/or binding dyes. In some embodiments, detecting a nucleic acid amplification product comprises use of dyes that specifically stain nucleic acid. For example, intercalating dyes exhibit enhanced fluorescence upon binding to DNA or RNA. Dyes may include DNA or RNA intercalating fluorophores and may include for example, SYTO® 82, acridine orange, ethidium bromide, Hoechst dyes, PicoGreen®, propidium iodide, SYBR® I (an asymmetrical cyanine dye), SYBR® II, TOTO (a thiaxole orange dimer) and YOYO (an oxazole yellow dimer). Dyes provide an opportunity for increasing the sensitivity of nucleic acid detection when used in conjunction with various detection methods. For example, ethidium bromide may be used for staining DNA in agarose gels after gel electrophoresis; propidium iodide and Hoechst 33258 may be used in flow cytometry to determine DNA ploidy of cells; SYBR® Green 1 may be used in the analysis of double-stranded DNA by capillary electrophoresis with laser induced fluorescence detection; and PicoGreen® may be used to enhance the detection of double-stranded DNA after matched ion pair polynucleotide chromatography.

In some embodiments, detecting a nucleic acid amplification product comprises use of absorbance methods (e.g., colorimetric, turbidity). In some instances, detection and/or quantitation of nucleic acid can be achieved by directly converting absorbance (e.g., UV absorbance measurements at 260 nm) to concentration, for example. Direct measurement of nucleic acid can be converted to concentration using the Beer Lambert law which relates absorbance to concentration using the path length of the measurement and an extinction coefficient. In some embodiments, detecting a nucleic acid amplification product comprises use of a colorimetric detection method. Any suitable colorimetric detection may be used, and non-limiting examples include assays that use nanoparticles (e.g., metallic nanoparticles, modified nanoparticles, unmodified nanoparticles) and/or peptide nucleic acid (PNA) probes. For example, certain gold nanoparticle-based methods typically rely on a quantitative coupling between target recognition and the aggregation of the nanoparticles, which, in turn, can lead to a change in the photonic properties (e.g., color) of a nanoparticle solution.

In some embodiments, detecting a nucleic acid amplification product comprises use of electrophoresis (e.g., gel electrophoresis, capillary electrophoresis). Gel electrophoresis involves the separation of nucleic acids through a matrix, generally a cross-linked polymer, using an electromotive force that pulls the molecules through the matrix. Molecules move through the matrix at different rates causing a separation between products that can be visualized and interpreted via a number of methods including but not limited to; autoradiography, phosphorimaging, and staining with nucleic acid chelating dyes. Capillary-gel electrophoresis (CGE) is a combination of traditional gel electrophoresis and liquid chromatography that employs a medium such as polyacrylamide in a narrow bore capillary to generate fast, high-efficient separations of nucleic acid molecules with up to single base resolution. CGE may be combined with laser induced fluorescence (LIF) detection where as few as six molecules of stained DNA can be detected. CGE/LIF detection generally involves the use of fluorescent DNA intercalating dyes including ethidium bromide, YOYO and SYBR® Green 1, and also may involve the use of fluorescent DNA derivatives where fluorescent dye is covalently bound to DNA. Simultaneous identification of several different target sequences (e.g., products from a multiplex reaction) may be made using this method.

In some embodiments, detecting a nucleic acid amplification product comprises use of mass spectrometry. Mass Spectrometry is an analytical technique that may be used to determine the structure and quantity of a nucleic acid and can be used to provide rapid analysis of complex mixtures. Following amplification, samples can be ionized, the resulting ions separated in electric and/or magnetic fields according to their mass-to-charge ratio, and a detector measures the mass-to-charge ratio of ions (Crain, P. F. and McCloskey, J. A., Current Opinion in Biotechnology 9: 25-34 (1998)). Mass spectrometry methods include, for example, MALDI, MALDI-TOF, or Electrospray. These methods may be combined with gas chromatography (GC/MS) and liquid chromatography (LC/MS). Mass spectrometry (e.g., matrix-assisted laser desorption/ionization mass spectrometry (MALDI MS)) can be high throughput due to high-speed signal acquisition and automated analysis off solid surfaces.

In some embodiments, detecting a nucleic acid amplification product comprises use of nucleic acid sequencing. The entire sequence or a partial sequence of an amplification product may be determined, and the determined nucleotide sequence may be referred to as a read. For example, linear amplification products may be analyzed directly without further amplification in some embodiments (e.g., by using single-molecule sequencing methodology). In certain embodiments, linear amplification products may be subject to further amplification and then analyzed (e.g., using sequencing by ligation or pyrosequencing methodology). Reads may be subject to different types of sequence analysis. Any suitable sequencing method can be utilized to detect, and in some instances determine the amount of, detectable products generated by the amplification methods described herein. Non-limiting examples of sequencing methods include single-end sequencing, paired-end sequencing, reversible terminator-based sequencing, sequencing by ligation, pyrosequencing, sequencing by synthesis, single-molecule sequencing, multiplex sequencing, solid phase single nucleotide sequencing, and nanopore sequencing.

In some embodiments, detecting a nucleic acid amplification product comprises use of digital amplification (e.g., digital PCR). Digital PCR, for example, takes advantage of nucleic acid (DNA, cDNA or RNA) amplification on a single molecule level, and offers a highly sensitive method for quantifying low copy number nucleic acid. Systems for digital amplification and analysis of nucleic acids are available (e.g., Fluidigm® Corporation).

Kits

Kits of may comprise, for example, one or more polymerases and one or more primers, and optionally one or more reverse transcriptases, as described herein. Where one target is amplified, a pair of primers (forward and reverse) may be included in the kit. Where multiple target sequences are amplified, a plurality of primer pairs may be included in the kit. A kit may include a control polynucleotide, and where multiple target sequences are amplified, a plurality of control polynucleotides may be included in the kit.

Kits may also comprise one or more of the components in any number of separate vessels, chambers, containers, packets, tubes, vials, microtiter plates and the like, or the components may be combined in various combinations in such containers. Components of the kit may, for example, be present in one or more containers. In some embodiments, all of the components are provided in one container. In some embodiments, the enzymes (e.g., polymerase(s) and/or reverse transcriptase(s)) may be provided in a separate container from the primers. The components may, for example, be lyophilized, freeze dried, or in a stable buffer. In one example, polymerase(s) and/or reverse transcriptase(s) are in lyophilized form in a single container, and the primers are either lyophilized, freeze dried, or in buffer, in a different container. In some embodiments, polymerase(s) and/or reverse transcriptase(s), and the primers are, in lyophilized form, in a single container.

Kits may further comprise, for example, dNTPs used in the reaction, or modified nucleotides, vessels, cuvettes or other containers used for the reaction, or a vial of water or buffer for re-hydrating lyophilized components. The buffer used may, for example, be appropriate for both polymerase and primer annealing activity.

Kits may also comprise instructions for performing one or more methods described herein and/or a description of one or more components described herein. Instructions and/or descriptions may be in printed form and may be included in a kit insert. A kit also may include a written description of an internet location that provides such instructions or descriptions.

Kits may further comprise reagents used for detection methods, such as, for example, reagents used for FRET, lateral flow devices, dipsticks, fluorescent dye, colloidal gold particles, latex particles, a molecular beacon, or polystyrene beads.

EXAMPLES

The examples set forth below illustrate certain embodiments and do not limit the technology.

Example 1: Detection of Chlamydia Trachomatis by Isothermal Amplification Technology In this example, the detection of nucleic acid from Chlamydia trachomatis is performed using isothermal amplification technology.

Real-Time Detection of Chlamydia Genomic DNA

A real-time assay for detection of chlamydia genomic DNA with fluorescent DNA dye was tested. In this assay, SYTO 82 was used, which is an orange fluorescent nucleic acid stain that exhibits bright orange fluorescence upon binding to nucleic acids. Master mix solutions were prepared with 20 mM Tris-HCl pH 8.8 at 25° C., 10 mM $(NH_4)_2SO_4$, 10 mM KCl, 4 mM $MgSO_4$, 0.1% Triton® X-100, 1 mM DTT, 2 µM SYTO 82, 0.25 mM dNTP, and 1 unit per reaction of modified 9 Degrees North (9°Nm™) DNA polymerase (New England BioLabs, Ipswich, Mass.). The amino acid sequence of 9°Nm™ DNA polymerase is set forth herein as SEQ ID NO:9. A primer set targeting a specific sequence within the 7,500 base pair C. trachomatis cryptic plasmid DNA was used, which included an 11 nucleotide forward primer (i.e., Ct_F11: 5'-GGCTTATG-GAG-3' (SEQ ID NO:1)) and a 10 nucleotide reverse primer (i.e., Ct_R10: 5'-ATACCGCTTA-3' (SEQ ID NO:2)). The assay was designed to generate 22 base DNA products which include a one base spacer. The spacer is a nucleotide between the 3' ends of the primers, and this nucleotide is not present in either of the primer sequences. The primers were each used at a final concentration 500 nM, and were mixed with either 2000 copies of chlamydia genomic DNA or Tris-EDTA buffer (TE) as a no target control (NTC). In certain instances, $dH_2O$ was used as a NTC. The primer mixtures were placed in separate reaction wells from the master mix solutions. The assay components were incubated at 65° C. for 2 minutes, and then combined to initiate the isothermal reaction. The results of the isothermal amplification reaction are presented in FIG. 1.

Electrospray Ionization Mass Spectrometry (ESI-MS) Confirmation of Specific Product Generation from Isothermal Amplification Reactions Amplification products generated from the isothermal amplification reactions described above were tested by Electrospray Ionization Mass Spectrometry (ESI-MS) to verify the specificity of the assay. The primers described above were each used at a final concentration 500 nM, and were mixed with either 20,000 copies of chlamydia genomic DNA or Tris-EDTA buffer (TE) as a no target control (NTC). In certain instances, $dH_2O$ was used as a NTC. The chlamydia genomic DNA was amplified at 65° C. for 10 minutes under the conditions described above. After amplification, the reactions were inactivated with Tris-EGTA (final 20 mM Tris-EGTA, $pH_{8.5}$). The reactions were then desalted and lyophilized before ESI-MS analysis.

Figure 2:
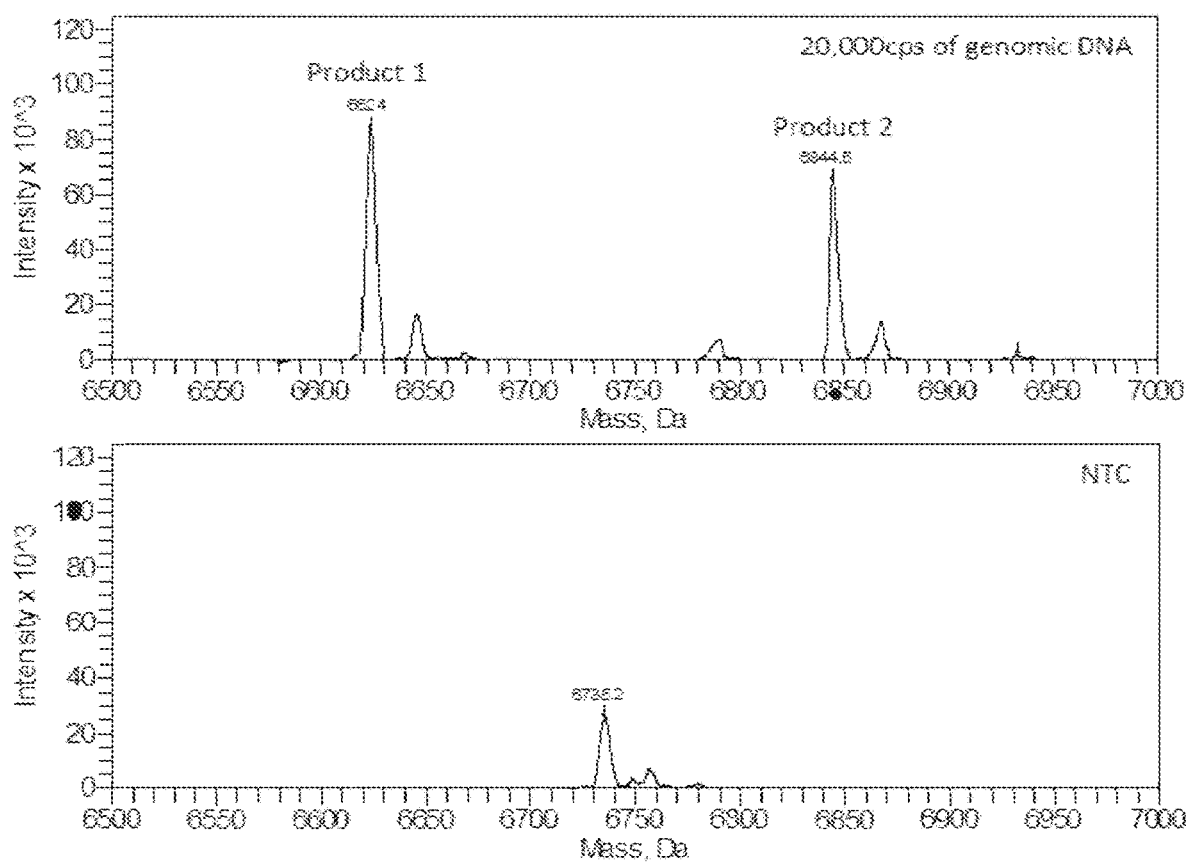
FIG. 2 shows Electrospray Ionization Mass Spectrometry (ESI-MS) detection of chlamydia genomic DNA assay products.

As shown in FIG. 2, ESI-MS results confirmed that the dominant products from the isothermal amplification of genomic DNA were specific 22-base products (i.e., 22-base forward product and 22-base reverse product). In comparison, the NTC reaction generated non-specific products with much less intensity than those with specific products.

Limit of Detection (LOD) for Chlamydia Genomic DNA Detection

Figure 3:
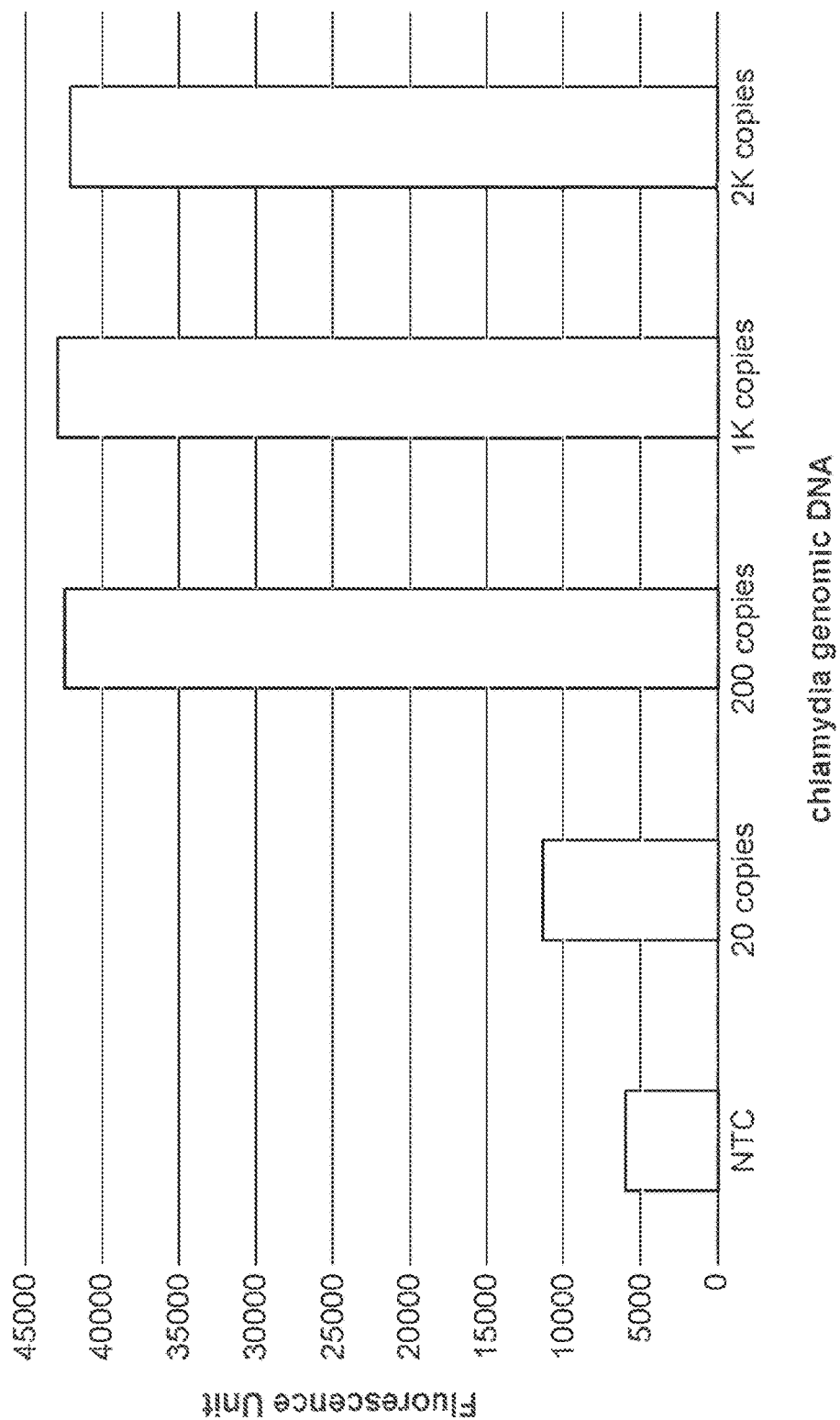
FIG. 3 shows chlamydia genomic DNA limit of detection (LOD) by endpoint molecular beacon detection.

Sensitivity of chlamydia genomic DNA detection was tested using an isothermal amplification assay. Under this approach, a 10 nucleotide primer assay under asymmetric amplification conditions was used for endpoint molecular beacon detection. A master mix solution was prepared with 20 mM Tris-HCl pH 8.8 at 25° C., 10 mM $(NH_4)_2SO_4$, 10 mM KCl, 4 mM $MgSO_4$, 0.1% Triton® X-100, 1 mM DTT, 0.25 mM dNTP, and 1 unit per reaction of modified 9 Degrees North (9°Nm™) DNA polymerase (New England BioLabs, Ipswich, Mass.). A primer set targeting a specific sequence within the 7,500 base pair C. trachomatis cryptic plasmid DNA was used, which included a 10 nucleotide forward primer (i.e., Ct_F10: 5'-GCTTATGGAG-3' (SEQ ID NO:3)) and a 10 nucleotide reverse primer (i.e., Ct_R10: 5'- ATACCGCTTA-3' (SEQ ID NO:2)). The assay was designed to generate a 21 base DNA product, which included a one base spacer. The spacer is a nucleotide between the 3' ends of the primers, and this nucleotide is not present in either of the primer sequences. The primers (i.e., 750 nM forward primer and 200 nM reverse primer) were mixed with either TE as a NTC or different amounts of chlamydia genomic DNA (i.e., 20 copies, 200 copies, 1,000 copies, 2,000 copies) and placed in separate reaction wells from the master mix solutions. In certain instances, $dH_2O$ was used as a NTC. The assay components were incubated at 65° C. for 2 minutes, then combined to initiate the isothermal reaction. The reactions were carried out for 10 minutes at 65° C., and then inactivated by placing on ice and adding EGTA. A molecular beacon (i.e., Ct FP MB5.18: Fam-CTGGCTACCGCTTAACTCCATAAGCCAG-3BHQ1 (SEQ ID NO:4)) containing a 20-base sequence complementary to the 21-base specific forward product was then added to each reaction well. The reaction products were detected by endpoint fluorescence readouts of the molecular beacon. As shown in FIG. 3, the isothermal reaction can amplify 20 copies of chlamydia genomic DNA to detectable levels in 10 minutes at 65° C. using endpoint detection of a molecular beacon.

Chlamydia Genomic DNA Real-Time Detection by Molecular Beacon

Figure 4:
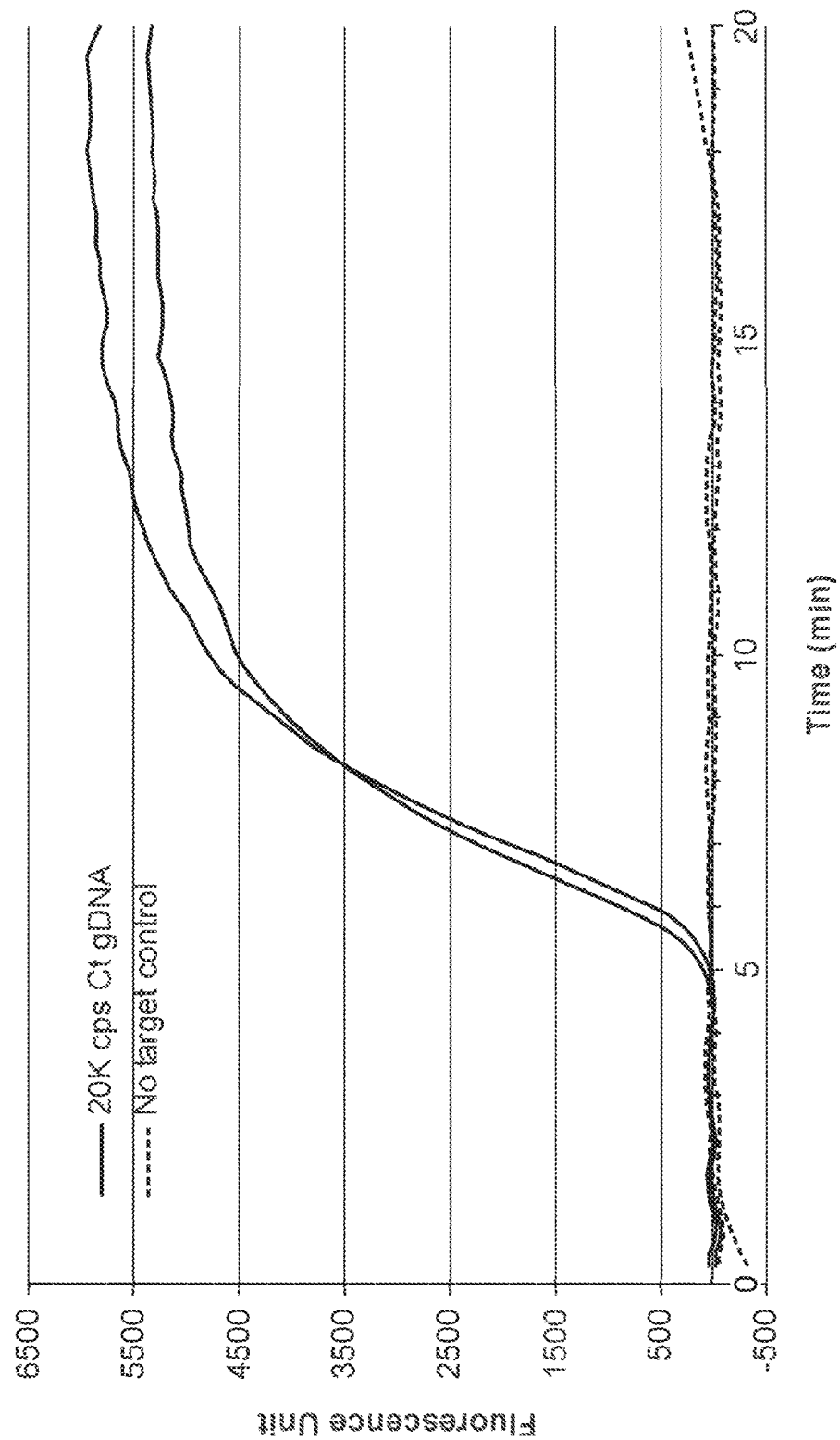
FIG. 4 shows chlamydia genomic DNA real-time detection by molecular beacon.
Figure 5:
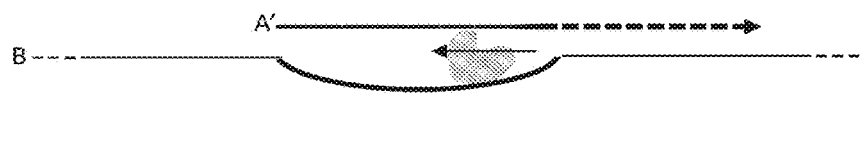
FIG. 5 shows a schematic of an isothermal amplification reaction described herein.
Figure 5:
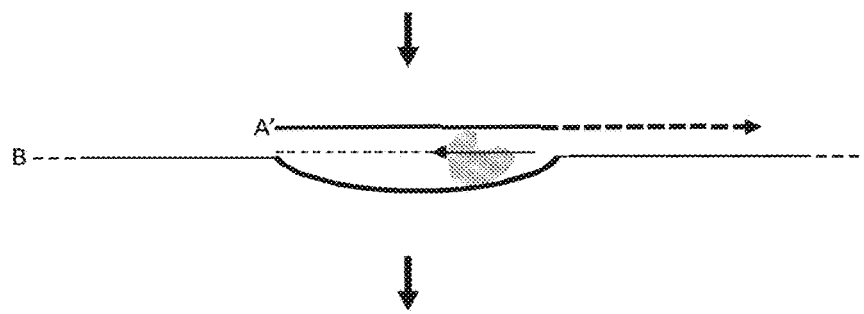
Figure 5:
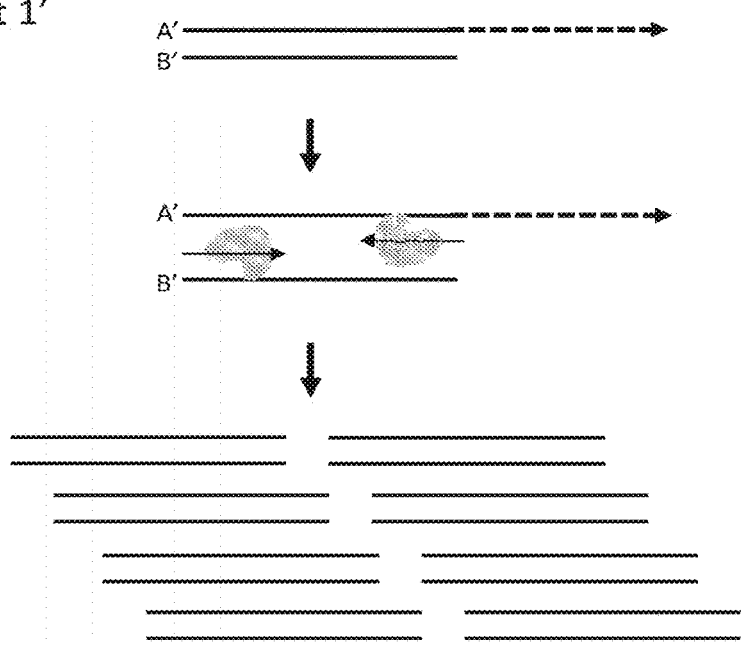

Another approach for real-time detection of chlamydia genomic DNA is to use molecular beacons for detection. Under this approach, a 10 nucleotide primer assay under asymmetric amplification conditions was used for real-time molecular beacon detection with $dH_2O$ or TE used as a no target control (NTC). Master mixes were prepared using 20 mM Tris-HCl pH 8.8 at 25° C., 10 mM $(NH_4)_2SO_4$, 10 mM KCl, 4 mM $MgSO_4$, 0.1% Triton® X-100, 50 nM fMB2 3PS (molecular beacon), 0.25 mM dNTP, and 1 unit/reaction of modified 9 Degrees North (9°Nm™) DNA polymerase (New England BioLabs, Ipswich, Mass.). The master mix included a molecular beacon (i.e., Ct_3PSMB.2: Fam-ccgcgagccttATACCGCTTAACTCg*c*g*g-IBFQ (SEQ ID NO:7)) which contained a 14-base sequence complementary to a portion of the forward product (14-base sequence is shown in upper case lettering). Nucleotides marked with * are phosphorothioate modified DNA bases. A primer set targeting a specific sequence within the 7,500 base pair *C. trachomatis* cryptic plasmid DNA was used, which included a 10 nucleotide forward primer (i.e., Ct_F10+2:5'- AGGCT-TATGG-3' (SEQ ID NO:5)) and a 10 nucleotide reverse primer (i.e., Ct_R10-2:5'-TTATACCGCT-3' (SEQ ID NO:6)). The assay was designed to generate a 25 base DNA product, which included a 5 base spacer. The spacer includes 5 nucleotides between the 3' ends of each primer, and these 5 nucleotides are not present in either of the primer sequences. The primers (i.e., 750 nM forward primer and 200 nM reverse primer) were combined with either TE as a NTC or 20,000 copies of chlamydia genomic DNA in reaction wells. In certain instances, dH$_2$O was used as a NTC. All components were incubated at 65° C. for 2 minutes, then combined to initiate the isothermal reaction carried out at 65° C. The reaction products were detected at various time points by real-time fluorescence readouts of the molecular beacon, as shown in FIG. 4.

Example 2: Examples of Sequences

Provided hereafter are non-limiting examples of certain nucleotide and amino acid sequences.

TABLE 1

Examples of sequences

| SEQ ID NO | Name | Type | Sequence |
|---|---|---|---|
| 1 | Ct_F11 | NA | GGCTTATGGAG |
| 2 | Ct_R10 | NA | ATACCGCTTA |
| 3 | Ct_F10 | NA | GCTTATGGAG |
| 4 | Ct FP MB5.18 | NA | CTGGCTACCGCTTAACTCCATAAGCCAG |
| 5 | Ct F10 +2 | NA | AGGCTTATGG |
| 6 | Ct R10 -2 | NA | TTATACCGCT |
| 7 | Ct_3PS MB.2 | NA | ccgcgagccttATACCGCTTAACTCg*c*g*g |
| 8 | 9° N | AA | MILDTDYITENGKPVIRVFKKENGEFKIEYDRTFEPYFYALLKDDSAIE DVKKVTAKRHGTVVKVKRAEKVQKKFLGRPIEVWKLYFNHPQDVPA IRDRIRAHPAVVDIYEYDIPFAKRYLIDKGLIPMEGDEELTMLAFDIETL YHEGEEFGTGPILMISYADGSEARVITWKKIDLPYVDVVSTEKEMIKR FLRVVREKDPDVLITYNGDNFDFAYLKKRCEELGIKFTLGRDGSEPK IQRMGDRFAVEVKGRIHFDLYPVIRRTINLPTYTLEAVYEAVFGKPKE KVYAEEIAQAWESGEGLERVARYSMEDAKVTYELGREFFPMEAQL SRLIGQSLWDVSRSSTGNLVEWFLLRKAYKRNELAPNKPDERELAR RRGGYAGGYVKEPERGLWDNIVYLDFRSLYPSIIITHNVSPDTLNRE GCKEYDVAPEVGHKFCKDFPGFIPSLLGDLLEERQKIKRKMKATVD PLEKKLLDYRQRAIKILANSFYGYYGYAKARWYCKECAESVTAWGR EYIEMVIRELEEKFGFKVLYADTDGLHATIPGADAETVKKKAKEFLKY INPKLPGLLELEYEGFYVRGFFVTKKKYAVIDEEGKITTRGLEIVRRD WSEIAKETQARVLEAILKHGDVEEAVRIVKEVTEKLSKYEVPPEKLVI HEQITRDLRDYKATGPHVAVAKRLAARGVKIRPGTVISYIVLKGSGRI GDRAIPADEFDPTKHRYDAEYYIENQVLPAVERILKAFGYRKEDLRY QKTKQVGLGAWLKVKGKK |
| 9 | 9° Nm™ | AA | MILDTDYITENGKPVIRVFKKENGEFKIEYDRTFEPYFYALLKDDSAIE DVKKVTAKRHGTVVKVKRAEKVQKKFLGRPIEVWKLYFNHPQDVPA IRDRIRAHPAVVDIYEYDIPFAKRYLIDKGLIPMEGDEELTMLAFDIDT LYHEGEEFGTGPILMISYADGSEARVITWKKIDLPYVDVVSTEKEMIK RFLRVVREKDPDVLITYNGDNFDFAYLKKRCEELGIKFTLGRDGSEP KIQRMGDRFAVEVKGRIHFDLYPVIRRTINLPTYTLEAVYEAVFGKPK EKVYAEEIAQAWESGEGLERVARYSMEDAKVTYELGREFFPMEAQ LSRLIGQSLWDVSRSSTGNLVEWFLLRKAYKRNELAPNKPDERELA RRRGGYAGGYVKEPERGLWDNIVYLDFRSLYPSIIITHNVSPDTLNR EGCKEYDVAPEVGHKFCKDFPGFIPSLLGDLLEERQKIKRKMKATV DPLEKKLLDYRQRAIKILANSFYGYYGYAKARWYCKECAESVTAWG REYIEMVIRELEEKFGFKVLYADTDGLHATIPGADAETVKKKAKEFLK YINPKLPGLLELEYEGFYVRGFFVTKKKYAVIDEEGKITTRGLEIVRR DWSEIAKETQARVLEAILKHGDVEEAVRIVKEVTEKLSKYEVPPEKL VIHEQITRDLRDYKATGPHVAVAKRLAARGVKIRPGTVISYIVLKGSG RIGDRAIPADEFDPTKHRYDAEYYIENQVLPAVERILKAFGYRKEDLR YQKTKQVGLGAWLKVKGKK |

*denotes phosphorothioate modified DNA bases

Example 3: Examples of Embodiments

The examples set forth below illustrate certain embodiments and do not limit the technology.

A1. A method for amplifying nucleic acid, comprising:
contacting non-denatured sample nucleic acid under isothermal amplification conditions with components comprising
a) at least one oligonucleotide, which at least one oligonucleotide comprises a polynucleotide complementary to a target sequence in the sample nucleic acid, and
b) at least one component providing hyperthermophile polymerase activity, thereby generating a nucleic acid amplification product.

A1.1 A method for amplifying nucleic acid, comprising:
contacting non-denatured sample nucleic acid under isothermal amplification conditions with
a) non-enzymatic components comprising at least one oligonucleotide, which at least one oligonucleotide comprises a polynucleotide complementary to a target sequence in the sample nucleic acid, and
b) an enzymatic component consisting of a hyperthermophile polymerase or a polymerase comprising an amino acid sequence that is at least about 90% identical to a hyperthermophile polymerase,
thereby generating a nucleic acid amplification product.

A1.2 A method for amplifying nucleic acid, comprising:
contacting non-denatured sample nucleic acid under isothermal amplification conditions with
a) non-enzymatic components comprising at least one oligonucleotide, which at least one oligonucleotide comprises a polynucleotide complementary to a target sequence in the sample nucleic acid, and
b) enzymatic activity consisting of i) hyperthermophile polymerase activity and, optionally, ii) reverse transcriptase activity,
thereby generating a nucleic acid amplification product.

A1.3 The method of embodiment A1.2, wherein the enzymatic activity consists of i) hyperthermophile polymerase activity, and ii) reverse transcriptase activity.

A2. The method of any one of embodiments A1 to A1.3, wherein the method does not comprise denaturing the sample nucleic acid prior to or during amplification.

A3. The method of any one of embodiments A1 to A2, wherein the sample nucleic acid is not contacted with an endonuclease prior to or during amplification.

A4. The method of any one of embodiments A1 to A3, wherein the sample nucleic acid is not contacted with an unwinding agent prior to or during amplification.

A5. The method of any one of embodiments A1 to A4, wherein the sample nucleic acid is not contacted with a helicase prior to or during amplification.

A5.1 The method of any one of embodiments A1 to A5, wherein the sample nucleic acid is not contacted with a recombinase prior to or during amplification.

A5.2 The method of any one of embodiments A1 to A5.1, wherein the sample nucleic acid is not contacted with a single-stranded DNA binding protein prior to or during amplification.

A6. The method of any one of embodiments A1 to A5.2, wherein the sample nucleic acid is unmodified prior to amplification.

A7. The method of embodiment A6, wherein the unmodified sample nucleic acid is from disrupted cells.

A8. The method of any one of embodiments A1 to A7, wherein the sample nucleic acid comprises DNA.

A9. The method of embodiment A8, wherein the sample nucleic acid comprises genomic DNA.

A10. The method of any one of embodiments A1 to A7, wherein the sample nucleic acid comprises RNA.

A11. The method of embodiment A10, wherein the sample nucleic acid comprises viral RNA.

A12. The method of embodiment A10, wherein the sample nucleic acid comprises bacterial RNA.

A13. The method of any one of embodiments A1 to A12, wherein the sample nucleic acid comprises single-stranded nucleic acid.

A14. The method of any one of embodiments A1 to A12, wherein the sample nucleic acid comprises double-stranded nucleic acid, which double-stranded nucleic acid comprises a first strand and a second strand.

A15. The method of any one of embodiments A1 to A14, wherein the at least one oligonucleotide comprises a first oligonucleotide and a second oligonucleotide.

A16. The method of any one of embodiments A1 to A14, wherein the at least one oligonucleotide consists of a first oligonucleotide and a second oligonucleotide.

A16.1 The method of embodiment A15 or A16, wherein the first oligonucleotide and the second oligonucleotide each comprise 8 to 16 bases.

A17. The method of embodiment A15, A16 or A16.1, wherein the first oligonucleotide comprises a first polynucleotide complementary to a target sequence in the first strand of the sample nucleic acid, and the second oligonucleotide comprises a second polynucleotide complementary to a target sequence in the second strand of the sample nucleic acid.

A18. The method of embodiment A15, A16 or A16.1, wherein the first oligonucleotide comprises a first polynucleotide continuously complementary to a target sequence in the first strand of the sample nucleic acid, and the second oligonucleotide comprises a second polynucleotide continuously complementary to a target sequence in the second strand of the sample nucleic acid.

A19. The method of embodiment A15, A16 or A16.1, wherein the first oligonucleotide consists of a first polynucleotide continuously complementary to a target sequence in the first strand of the sample nucleic acid, and the second oligonucleotide consists of a second polynucleotide continuously complementary to a target sequence in the second strand of the sample nucleic acid.

A20. The method of any one of embodiments A1 to A19, wherein sample nucleic acid is obtained from a subject prior to amplification.

A21. The method of any one of embodiments A1 to A20, wherein unpurified sample nucleic acid is amplified.

A22. The method of any one of embodiments A1 to A20, wherein purified sample nucleic acid is amplified.

A23. The method of any one of embodiments A1 to A20, further comprising purifying sample nucleic acid prior to amplification.

A24. The method of any one of embodiments A1 to A23, wherein the hyperthermophile polymerase activity is provided by a hyperthermophile polymerase or functional fragment thereof.

A25. The method of any one of embodiments A1 to A23, wherein the hyperthermophile polymerase activity is provided by a polymerase comprising an amino acid sequence that is at least about 90% identical to a hyperthermophile polymerase or functional fragment thereof.

A26. The method of any one of embodiments A1 to A23, wherein the hyperthermophile polymerase activity is provided by an Archaea hyperthermophile polymerase or functional fragment thereof.

A27. The method of any one of embodiments A1 to A26, wherein the hyperthermophile polymerase activity is provided by a polymerase comprising an amino acid sequence of SEQ ID NO:8 or functional fragment thereof.

A28. The method of any one of embodiments A1 to A26, wherein the hyperthermophile polymerase activity is provided by a polymerase comprising an amino acid sequence that is at least about 90% identical to the amino acid sequence of SEQ ID NO:8 or functional fragment thereof.

A28.1 The method of any one of embodiments A1 to A28, wherein the hyperthermophile polymerase activity is provided by a polymerase having low exonuclease activity.

A28.2 The method of any one of embodiments A1 to A28, wherein the hyperthermophile polymerase activity is provided by a polymerase having no exonuclease activity.

A29. The method of any one of embodiments A1 to A28.2, wherein the amplification is performed at a constant temperature of about 55 degrees Celsius to about 75 degrees Celsius.

A30. The method of any one of embodiments A1 to A28.2, wherein the amplification is performed at a constant temperature of about 55 degrees Celsius to about 65 degrees Celsius.

A31. The method of any one of embodiments A1 to A28.2, wherein the amplification is performed at a constant temperature of about 65 degrees Celsius.

A32. The method of any one of embodiments A1 to A28.2, wherein the amplification is performed at a constant temperature of about 60 degrees Celsius.

A33. The method of any one of embodiments A1 to A32, wherein the nucleic acid amplification product is detectable in 10 minutes or less.

A34. The method of any one of embodiments A1 to A33, wherein the nucleic acid amplification product comprises a polynucleotide that is continuously complementary to or substantially identical to a target sequence in the sample nucleic acid.

A35. The method of any one of embodiments A1 to A33, wherein the nucleic acid amplification product consists of a polynucleotide that is continuously complementary to or substantially identical to a target sequence in the sample nucleic acid.

A36. The method of any one of embodiments A1 to A35, wherein the nucleic acid amplification product is about 20 to 40 bases long.

A37. The method of any one of embodiments A16 to A36, wherein the nucleic acid amplification product comprises i) a first nucleotide sequence that is continuously complementary to or substantially identical to the first polynucleotide of the first oligonucleotide, ii) a second nucleotide sequence that is continuously complementary to or substantially identical to the second polynucleotide of the second oligonucleotide, and iii) a spacer sequence, wherein the spacer sequence is flanked by the first nucleotide sequence and the second nucleotide sequence.

A38. The method of any one of embodiments A16 to A36, wherein the nucleic acid amplification product consists of i) a first nucleotide sequence that is continuously complementary to or substantially identical to the first polynucleotide of the first oligonucleotide, ii) a second nucleotide sequence that is continuously complementary to or substantially identical to the second polynucleotide of the second oligonucleotide, and iii) a spacer sequence, wherein the spacer sequence is flanked by the first nucleotide sequence and the second nucleotide sequence.

A39. The method of embodiment A37 or A38, wherein the spacer sequence comprises 1 to 10 bases.

A40. The method of embodiment A37 or A38, wherein the spacer sequence comprises 1 to 5 bases.

A41. The method of any one of embodiments A37 to A40, wherein the spacer sequence is not complementary to or identical to the first polynucleotide of the first oligonucleotide and is not complementary to or identical to the second polynucleotide of the second oligonucleotide.

A42. The method of any one of embodiments A37 to A41, wherein the spacer sequence is continuously complementary to or substantially identical to a portion of a target sequence in the sample nucleic acid.

A43. The method of any one of embodiments A1 to A42, further comprising detecting the nucleic acid amplification product.

A44. The method of embodiment A43, wherein detecting the nucleic acid amplification product is performed in 10 minutes or less from the time the sample nucleic acid is contacted with the component providing the hyperthermophile polymerase activity and the at least one oligonucleotide.

A45. The method of embodiment A43 or A44, wherein detecting the nucleic acid amplification product comprises use of a real-time detection method.

A46. The method of embodiment A43, A44 or A45, wherein detecting the nucleic acid amplification product comprises detection of a fluorescent signal.

A47. The method of embodiment A46, wherein the fluorescent signal is from a molecular beacon.

A48. The method of any one of embodiments A1 to A47, further comprising contacting the nucleic acid amplification product with a signal generating oligonucleotide that comprises i) a polynucleotide complementary to a sequence in the amplification product, and ii) a fluorophore and a quencher.

A49. The method of any one of embodiments A1 to A47, wherein one or more of the at least one oligonucleotide comprise a polynucleotide not complementary to a sequence in the sample nucleic acid that hybridizes to a signal generating oligonucleotide, and wherein the method further comprises contacting the amplification product with the signal generating oligonucleotide that comprises a fluorophore and a quencher.

A50. The method of any one of embodiments A1 to A49, wherein the method is performed in a single reaction volume.

A51. The method of any one of embodiments A1 to A50, wherein the method is performed in a single reaction vessel.

A52. The method of any one of embodiments A1 to A51, comprising multiplex amplification.

B1. A method for processing nucleic acid, comprising:
amplifying nucleic acid, wherein the amplifying consists essentially of contacting non-denatured sample nucleic acid under isothermal amplification conditions with
a) at least one oligonucleotide, which at least one oligonucleotide comprises a polynucleotide complementary to a target sequence in the sample nucleic acid, and
b) at least one component providing hyperthermophile polymerase activity, thereby generating a nucleic acid amplification product.

B2. A method for processing nucleic acid, comprising:
amplifying nucleic acid, wherein the amplifying consists essentially of contacting non-denatured sample nucleic acid under isothermal amplification conditions with
a) non-enzymatic components comprising at least one oligonucleotide, which at least one oligonucleotide comprises a polynucleotide complementary to a target sequence in the sample nucleic acid, and
b) an enzymatic component consisting of a hyperthermophile polymerase or a polymerase comprising an amino acid sequence that is at least about 90% identical to a hyperthermophile polymerase,
thereby generating a nucleic acid amplification product.

B3. A method for processing nucleic acid, comprising:
amplifying nucleic acid, wherein the amplifying consists essentially of contacting non-denatured sample nucleic acid under isothermal amplification conditions with
a) non-enzymatic components comprising at least one oligonucleotide, which at least one oligonucleotide comprises a polynucleotide complementary to a target sequence in the sample nucleic acid, and
b) enzymatic activity consisting of i) hyperthermophile polymerase activity and, optionally, ii) reverse transcriptase activity,
thereby generating a nucleic acid amplification product.

B4. The method of embodiment B3, wherein the enzymatic activity consists of i) hyperthermophile polymerase activity, and ii) reverse transcriptase activity.

B5. A method for processing nucleic acid, comprising:
amplifying nucleic acid, wherein the amplifying consists of contacting non-denatured sample nucleic acid under isothermal amplification conditions with
a) at least one oligonucleotide, which at least one oligonucleotide comprises a polynucleotide complementary to a target sequence in the sample nucleic acid, and
b) at least one component providing hyperthermophile polymerase activity, thereby generating a nucleic acid amplification product.

B6. A method for processing nucleic acid, comprising:
amplifying nucleic acid, wherein the amplifying consists of contacting non-denatured sample nucleic acid under isothermal amplification conditions with
a) non-enzymatic components comprising at least one oligonucleotide, which at least one oligonucleotide comprises a polynucleotide complementary to a target sequence in the sample nucleic acid, and
b) an enzymatic component consisting of a hyperthermophile polymerase or a polymerase comprising an amino acid sequence that is at least about 90% identical to a hyperthermophile polymerase,
thereby generating a nucleic acid amplification product.

B7. A method for processing nucleic acid, comprising:
amplifying nucleic acid, wherein the amplifying consists of contacting non-denatured sample nucleic acid under isothermal amplification conditions with
a) non-enzymatic components comprising at least one oligonucleotide, which at least one oligonucleotide comprises a polynucleotide complementary to a target sequence in the sample nucleic acid, and
b) enzymatic activity consisting of i) hyperthermophile polymerase activity and, optionally, ii) reverse transcriptase activity,
thereby generating a nucleic acid amplification product.

B8. The method of embodiment B7, wherein the enzymatic activity consists of i) hyperthermophile polymerase activity, and ii) reverse transcriptase activity.

B9. The method of any one of embodiments B1 to B8, wherein the sample nucleic acid is unmodified prior to amplification.

B10. The method of embodiment B9, wherein the unmodified sample nucleic acid is from disrupted cells.

B11. The method of any one of embodiments B1 to B10, wherein the sample nucleic acid comprises DNA.

B12. The method of embodiment B11, wherein the sample nucleic acid comprises genomic DNA.

B13. The method of any one of embodiments B1 to B10, wherein the sample nucleic acid comprises RNA.

B14. The method of embodiment B13, wherein the sample nucleic acid comprises viral RNA.

B15. The method of embodiment B13, wherein the sample nucleic acid comprises bacterial RNA.

B16. The method of any one of embodiments B1 to B15, wherein the sample nucleic acid comprises single-stranded nucleic acid.

B17. The method of any one of embodiments B1 to B15, wherein the sample nucleic acid comprises double-stranded nucleic acid, which double-stranded nucleic acid comprises a first strand and a second strand.

B18. The method of any one of embodiments B1 to B17, wherein the at least one oligonucleotide comprises a first oligonucleotide and a second oligonucleotide.

B19. The method of any one of embodiments B1 to B17, wherein the at least one oligonucleotide consists of a first oligonucleotide and a second oligonucleotide.

B19.1 The method of embodiment B18 or B19, wherein the first oligonucleotide and the second oligonucleotide each comprise 8 to 16 bases.

B20. The method of embodiment B18, B19 or B19.1, wherein the first oligonucleotide comprises a first polynucleotide complementary to a target sequence in the first strand of the sample nucleic acid, and the second oligonucleotide comprises a second polynucleotide complementary to a target sequence in the second strand of the sample nucleic acid.

B21. The method of embodiment B18, B19 or B19.1, wherein the first oligonucleotide comprises a first polynucleotide continuously complementary to a target sequence in the first strand of the sample nucleic acid, and the second oligonucleotide comprises a second polynucleotide continuously complementary to a target sequence in the second strand of the sample nucleic acid.

B22. The method of embodiment B18, B19 or B19.1, wherein the first oligonucleotide consists of a first polynucleotide continuously complementary to a target sequence in the first strand of the sample nucleic acid, and the second oligonucleotide consists of a second polynucleotide continuously complementary to a target sequence in the second strand of the sample nucleic acid.

B23. The method of any one of embodiments B1 to B22, wherein sample nucleic acid is obtained from a subject prior to amplification.

B24. The method of any one of embodiments B1 to B22, wherein unpurified sample nucleic acid is amplified.

B25. The method of any one of embodiments B1 to B22, wherein purified sample nucleic acid is amplified.

B26. The method of any one of embodiments B1 to B22, further comprising purifying sample nucleic acid prior to amplification.

B27. The method of any one of embodiments B1 to B26, wherein the hyperthermophile polymerase activity is provided by a hyperthermophile polymerase or functional fragment thereof.

B28. The method of any one of embodiments B1 to B26, wherein the hyperthermophile polymerase activity is provided by a polymerase comprising an amino acid sequence that is at least about 90% identical to a hyperthermophile polymerase or functional fragment thereof.

B29. The method of any one of embodiments B1 to B26, wherein the hyperthermophile polymerase activity is provided by an Archaea hyperthermophile polymerase or functional fragment thereof.

B30. The method of any one of embodiments B1 to B29, wherein the hyperthermophile polymerase activity is provided by a polymerase comprising an amino acid sequence of SEQ ID NO:8 or functional fragment thereof.

B31. The method of any one of embodiments B1 to B29, wherein the hyperthermophile polymerase activity is provided by a polymerase comprising an amino acid sequence that is at least about 90% identical to the amino acid sequence of SEQ ID NO:8 or functional fragment thereof.

B31.1 The method of any one of embodiments B1 to B31, wherein the hyperthermophile polymerase activity is provided by a polymerase having low exonuclease activity.

B32.2 The method of any one of embodiments B1 to B31, wherein the hyperthermophile polymerase activity is provided by a polymerase having no exonuclease activity.

B32. The method of any one of embodiments B1 to B31.2, wherein the amplification is performed at a constant temperature of about 55 degrees Celsius to about 75 degrees Celsius.

B33. The method of any one of embodiments B1 to B31.2, wherein the amplification is performed at a constant temperature of about 55 degrees Celsius to about 65 degrees Celsius.

B34. The method of any one of embodiments B1 to B31.2, wherein the amplification is performed at a constant temperature of about 65 degrees Celsius.

B35. The method of any one of embodiments B1 to B31.2, wherein the amplification is performed at a constant temperature of about 60 degrees Celsius.

B36. The method of any one of embodiments B1 to B35, wherein the nucleic acid amplification product is detectable in 10 minutes or less.

B37. The method of any one of embodiments B1 to B36, wherein the nucleic acid amplification product comprises a polynucleotide that is continuously complementary to or substantially identical to a target sequence in the sample nucleic acid.

B38. The method of any one of embodiments B1 to B36, wherein the nucleic acid amplification product consists of a polynucleotide that is continuously complementary to or substantially identical to a target sequence in the sample nucleic acid.

B39. The method of any one of embodiments B1 to B38, wherein the nucleic acid amplification product is about 20 to 40 bases long.

B40. The method of any one of embodiments B20 to B39, wherein the nucleic acid amplification product comprises i) a first nucleotide sequence that is continuously complementary to or substantially identical to the first polynucleotide of the first oligonucleotide, ii) a second nucleotide sequence that is continuously complementary to or substantially identical to the second polynucleotide of the second oligonucleotide, and iii) a spacer sequence, wherein the spacer sequence is flanked by the first nucleotide sequence and the second nucleotide sequence.

B41. The method of any one of embodiments B20 to B39, wherein the nucleic acid amplification product consists of i) a first nucleotide sequence that is continuously complementary to or substantially identical to the first polynucleotide of the first oligonucleotide, ii) a second nucleotide sequence that is continuously complementary to or substantially identical to the second polynucleotide of the second oligonucleotide, and iii) a spacer sequence, wherein the spacer sequence is flanked by the first nucleotide sequence and the second nucleotide sequence.

B42. The method of embodiment B40 or B41, wherein the spacer sequence comprises 1 to 10 bases.

B43. The method of embodiment B40 or B41, wherein the spacer sequence comprises 1 to 5 bases.

B44. The method of any one of embodiments B40 to B43, wherein the spacer sequence is not complementary to or identical to the first polynucleotide of the first oligonucleotide and is not complementary to or identical to the second polynucleotide of the second oligonucleotide.

B45. The method of any one of embodiments B40 to B44, wherein the spacer sequence is continuously complementary to or substantially identical to a portion of a target sequence in the sample nucleic acid.

B46. The method of any one of embodiments B1 to B45, further comprising detecting the nucleic acid amplification product.

B47. The method of embodiment B46, wherein detecting the nucleic acid amplification product is performed in 10 minutes or less from the time the sample nucleic acid is contacted with the component providing the hyperthermophile polymerase activity and the at least one oligonucleotide.

B48. The method of embodiment B46 or B47, wherein detecting the nucleic acid amplification product comprises use of a real-time detection method.

B49. The method of embodiment B46, B47 or B48, wherein detecting the nucleic acid amplification product comprises detection of a fluorescent signal.

B50. The method of embodiment B49, wherein the fluorescent signal is from a molecular beacon.

B51. The method of any one of embodiments B1 to B50, further comprising contacting the nucleic acid amplification product with a signal generating oligonucleotide that comprises i) a polynucleotide complementary to a sequence in the amplification product, and ii) a fluorophore and a quencher.

B52. The method of any one of embodiments B1 to B50, wherein one or more of the at least one oligonucleotide comprise a polynucleotide not complementary to a sequence in the sample nucleic acid that hybridizes to a signal generating oligonucleotide, and wherein the method further comprises contacting the amplification product with the signal generating oligonucleotide that comprises a fluorophore and a quencher.

B53. The method of any one of embodiments B1 to B52, wherein the method is performed in a single reaction volume.

B54. The method of any one of embodiments B1 to B53, wherein the method is performed in a single reaction vessel.

B55. The method of any one of embodiments B1 to B54, comprising multiplex amplification.

C1. A method for determining the presence, absence or amount of a target sequence in sample nucleic acid, comprising:
  a) amplifying a target sequence in the sample nucleic acid, wherein:
the target sequence comprises a first strand and a second strand, the first strand and second strand are complementary to each other, and the amplifying comprises contacting non-denatured sample nucleic acid under helicase-free isothermal amplification conditions with:
  i) a first oligonucleotide and a second oligonucleotide, wherein the first oligonucleotide comprises a first polynucleotide continuously complementary to a sequence in the first strand, and the second oligonucleotide comprises a second polynucleotide continuously complementary to a sequence in the second strand; and
  ii) at least one component providing a hyperthermophile polymerase activity, thereby generating a nucleic acid amplification product, wherein the nucleic acid amplification product comprises 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases, and
the spacer sequence is flanked by the first nucleotide sequence and the second nucleotide sequence; and
  b) detecting the nucleic acid amplification product, wherein detecting the nucleic acid amplification product comprises use of a real-time detection method and is performed in 10 minutes or less from the time the sample nucleic acid is contacted with (a)(i) and (a)(ii), whereby the presence, absence or amount of a target sequence in sample nucleic acid is determined.

C1.1 The method of embodiment C1, wherein the first oligonucleotide consists essentially of a first polynucleotide continuously complementary to a sequence in the first strand, and the second oligonucleotide consists essentially of a second polynucleotide continuously complementary to a sequence in the second strand; and/or the nucleic acid amplification product consists essentially of 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases.

C1.2 The method of embodiment C1, wherein the first oligonucleotide consists of a first polynucleotide continuously complementary to a sequence in the first strand, and the second oligonucleotide consists of a second polynucleotide continuously complementary to a sequence in the second strand; and/or the nucleic acid amplification product consists of 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases.

C1.3 A method for determining the presence, absence or amount of a target sequence in sample nucleic acid, comprising:
  a) amplifying a target sequence in the sample nucleic acid, wherein: the target sequence comprises a first strand and a second strand, the first strand and second strand are complementary to each other, and the amplifying comprises contacting non-denatured sample nucleic acid under helicase-free isothermal amplification conditions with:
    i) a first oligonucleotide and a second oligonucleotide, wherein the first oligonucleotide consists of a first polynucleotide continuously complementary to a sequence in the first strand, and the second oligonucleotide consists of a second polynucleotide continuously complementary to a sequence in the second strand; and
    ii) at least one component providing a hyperthermophile polymerase activity, thereby generating a nucleic acid amplification product, wherein the nucleic acid amplification product consists of 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases, and
    the spacer sequence is flanked by the first nucleotide sequence and the second nucleotide sequence; and
  b) detecting the nucleic acid amplification product, wherein detecting the nucleic acid amplification product comprises use of a real-time detection method and is performed in 10 minutes or less from the time the sample nucleic acid is contacted with (a)(i) and (a)(ii), whereby the presence, absence or amount of a target sequence in sample nucleic acid is determined.

C1.4 The method of any one of embodiments C1 to C1.3, wherein the amplifying comprises contacting non-denatured sample nucleic acid under helicase-free and recombinase-free isothermal amplification conditions.

C2. The method of any one of embodiments C1 to C1.4, wherein the at least one component providing a hyperthermophile polymerase activity comprises a hyperthermophile polymerase or functional fragment thereof, or a polymerase comprising an amino acid sequence that is at least about 90% identical to a hyperthermophile polymerase or functional fragment thereof.

C3. The method of any one of embodiments C1 to C1.4, wherein the at least one component providing a hyperthermophile polymerase activity consists of a hyperthermophile polymerase or functional fragment thereof, or a polymerase comprising an amino acid sequence that is at least about 90% identical to a hyperthermophile polymerase or functional fragment thereof.

C4. The method of any one of embodiments C1 to C3, wherein the hyperthermophile polymerase activity is provided by an Archaea hyperthermophile polymerase or functional fragment thereof.

C5. The method of any one of embodiments C1 to C4, wherein the hyperthermophile polymerase activity is provided by a polymerase comprising an amino acid sequence of SEQ ID NO:8 or functional fragment thereof.

C6. The method of any one of embodiments C1 to C4, wherein the hyperthermophile polymerase activity is provided by a polymerase comprising an amino acid sequence that is at least about 90% identical to the amino acid sequence of SEQ ID NO:8 or functional fragment thereof.

C6.1 The method of any one of embodiments C1 to C6, wherein the hyperthermophile polymerase activity is provided by a polymerase having low exonuclease activity.

C6.2 The method of any one of embodiments C1 to C6, wherein the hyperthermophile polymerase activity is provided by a polymerase having no exonuclease activity.

C7. The method of any one of embodiments C1 to C6.2, wherein part (a)(ii) further comprises at least one component providing a reverse transcriptase activity.

C8. The method of any one of embodiments C1 to C6.2, wherein the at least one component providing hyperthermophile polymerase activity further provides a reverse transcriptase activity.

C8.1 The method of any one of embodiments C1 to C8, wherein the first oligonucleotide and the second oligonucleotide each comprise 8 to 16 bases.

C9. The method of any one of embodiments C1 to C8.1, wherein the method does not comprise denaturing the sample nucleic acid prior to or during amplification.

C10. The method of any one of embodiments C1 to C9, wherein the sample nucleic acid is not contacted with an endonuclease prior to, during, or following amplification.

C10.1 The method of any one of embodiments C1 to C10, wherein the sample nucleic acid is not contacted with a recombinase prior to or during amplification.

C10.2 The method of any one of embodiments C1 to C10.1, wherein the sample nucleic acid is not contacted with a single-stranded DNA binding protein prior to or during amplification.

C11. The method of any one of embodiments C1 to C10.2, wherein the sample nucleic acid is unmodified prior to amplification.

C12. The method of embodiment C11, wherein the unmodified sample nucleic acid is from disrupted cells.

C13. The method of any one of embodiments C1 to C12, wherein the sample nucleic acid comprises DNA.

C14. The method of embodiment C13, wherein the sample nucleic acid comprises genomic DNA.

C15. The method of any one of embodiments C1 to C12, wherein the sample nucleic acid comprises RNA.

C16. The method of embodiment C15, wherein the sample nucleic acid comprises viral RNA.

C17. The method of embodiment C15, wherein the sample nucleic acid comprises bacterial RNA.

C18. The method of any one of embodiments C1 to C17, wherein the sample nucleic acid comprises single-stranded nucleic acid.

C19. The method of any one of embodiments C1 to C17, wherein the sample nucleic acid comprises double-stranded nucleic acid.

C20. The method of any one of embodiments C1 to C19, wherein sample nucleic acid is obtained from a subject prior to amplification.

C20.1 The method of any one of embodiments C1 to C20, wherein unpurified sample nucleic acid is amplified.

C20.2 The method of any one of embodiments C1 to C20, wherein purified sample nucleic acid is amplified.

C21. The method of any one of embodiments C1 to C20.2, further comprising purifying sample nucleic acid prior to amplification.

C22. The method of any one of embodiments C1 to C21, wherein the amplification is performed at a constant temperature of about 55 degrees Celsius to about 75 degrees Celsius.

C23. The method of any one of embodiments C1 to C21, wherein the amplification is performed at a constant temperature of about 55 degrees Celsius to about 65 degrees Celsius.

C24. The method of any one of embodiments C1 to C21, wherein the amplification is performed at a constant temperature of about 65 degrees Celsius.

C25. The method of any one of embodiments C1 to C21, wherein the amplification is performed at a constant temperature of about 60 degrees Celsius.

C26. The method of any one of embodiments C1 to C25, wherein the nucleic acid amplification product is about 20 to 40 bases long.

C27. The method of any one of embodiments C1 to C26, wherein the spacer sequence comprises 1 to 5 bases.

C28. The method of any one of embodiments C1 to C27, wherein the spacer sequence is not complementary to or identical to the first polynucleotide of the first oligonucleotide and is not complementary to or identical to the second polynucleotide of the second oligonucleotide.

C29. The method of any one of embodiments C1 to C28, wherein the spacer sequence is continuously complementary to or substantially identical to a portion of a target sequence in the sample nucleic acid.

C30. The method of any one of embodiments C1 to C28, wherein detecting the nucleic acid amplification product comprises detection of a fluorescent signal.

C31. The method embodiment C30, wherein the fluorescent signal is from a molecular beacon.

C32. The method of any one of embodiments C1 to C31, further comprising contacting the nucleic acid amplification product with a signal generating oligonucleotide that comprises i) a polynucleotide complementary to a sequence in the amplification product, and ii) a fluorophore and a quencher.

C33. The method of any one of embodiments C1 to C32, wherein the method is performed in a single reaction volume.

C34. The method of any one of embodiments C1 to C33, wherein the method is performed in a single reaction vessel.

C35. The method of any one of embodiments C1 to C34, comprising multiplex amplification.

D1. A kit for determining the presence, absence or amount of a target sequence in sample nucleic acid comprising:
  a) components for amplifying a target sequence in the sample nucleic acid under helicase-free isothermal amplification conditions, which components comprise:
    i) a first oligonucleotide and a second oligonucleotide, wherein the first oligonucleotide comprises a first polynucleotide continuously complementary to a sequence in a first strand of the target sequence, and the second oligonucleotide comprises a second polynucleotide continuously complementary to a sequence in a second strand of the target sequence, which first strand and second strand of the target sequence are complementary to each other; and
    ii) at least one component providing a hyperthermophile polymerase activity; and
  b) at least one component providing real-time detection activity for a nucleic acid amplification product.

D1.1 The kit of embodiment D1, wherein the first oligonucleotide consists essentially of a first polynucleotide continuously complementary to a sequence in a first strand of the target sequence, and the second oligonucleotide consists essentially of a second polynucleotide continuously complementary to a sequence in a second strand of the target sequence.

D1.2 The kit of embodiment D1, wherein the first oligonucleotide consists of a first polynucleotide continuously complementary to a sequence in a first strand of the target sequence, and the second oligonucleotide consists of a second polynucleotide continuously complementary to a sequence in a second strand of the target sequence.

D1.3 A kit for determining the presence, absence or amount of a target sequence in sample nucleic acid comprising:
- a) components for amplifying a target sequence in the sample nucleic acid under helicase-free isothermal amplification conditions, which components comprise:
  - i) a first oligonucleotide and a second oligonucleotide, wherein the first oligonucleotide consists of a first polynucleotide continuously complementary to a sequence in a first strand of the target sequence, and the second oligonucleotide consists of a second polynucleotide continuously complementary to a sequence in a second strand of the target sequence, which first strand and second strand of the target sequence are complementary to each other; and
  - ii) at least one component providing a hyperthermophile polymerase activity; and
- b) at least one component providing real-time detection activity for a nucleic acid amplification product.

D1.4 The kit of any one of embodiments D1 to D1.3, wherein the sample nucleic acid is amplified under helicase-free and recombinase-free isothermal amplification conditions.

D2. The kit of any one of embodiments D1 to D1.4, wherein the at least one component providing a hyperthermophile polymerase activity comprises a hyperthermophile polymerase or functional fragment thereof, or a polymerase comprising an amino acid sequence that is at least about 90% identical to a hyperthermophile polymerase or functional fragment thereof.

D3. The kit of any one of embodiments D1 to D1.4, wherein the at least one component providing a hyperthermophile polymerase activity consists of a hyperthermophile polymerase or functional fragment thereof, or a polymerase comprising an amino acid sequence that is at least about 90% identical to a hyperthermophile polymerase or functional fragment thereof.

D4. The kit of any one of embodiments D1 to D3, wherein the hyperthermophile polymerase activity is provided by an Archaea hyperthermophile polymerase or functional fragment thereof.

D5. The kit of any one of embodiments D1 to D4, wherein the hyperthermophile polymerase activity is provided by a polymerase comprising an amino acid sequence of SEQ ID NO:8 or functional fragment thereof.

D6. The kit of any one of embodiments D1 to D4, wherein the hyperthermophile polymerase activity is provided by a polymerase comprising an amino acid sequence that is at least about 90% identical to the amino acid sequence of SEQ ID NO:8 or functional fragment thereof.

D7. The kit of any one of embodiments D1 to D6, wherein the hyperthermophile polymerase activity is provided by a polymerase having low exonuclease activity.

D8. The kit of any one of embodiments D1 to D6, wherein the hyperthermophile polymerase activity is provided by a polymerase having no exonuclease activity.

D9. The kit of any one of embodiments D1 to D8, wherein part (a)(ii) further comprises at least one component providing a reverse transcriptase activity.

D10. The kit of any one of embodiments D1 to D8, wherein the at least one component providing hyperthermophile polymerase activity further provides a reverse transcriptase activity.

D11. The kit of any one of embodiments D1 to D10, wherein the first oligonucleotide and the second oligonucleotide each comprise 8 to 16 bases.

D12. The kit of any one of embodiments D1 to D11, wherein the real-time detection activity is provided by a molecular beacon.

D13. The kit of any one of embodiments D1 to D12, further comprising instructions for carrying out a method for determining the presence, absence or amount of a target sequence in sample nucleic acid, the method comprising:
- a) amplifying a target sequence in the sample nucleic acid, wherein:
  the target sequence comprises a first strand and a second strand,
  the first strand and second strand are complementary to each other,
  and the amplifying comprises contacting non-denatured sample nucleic acid under helicase-free isothermal amplification conditions with:
  - i) a first oligonucleotide and a second oligonucleotide, wherein the first oligonucleotide comprises a first polynucleotide continuously complementary to a sequence in the first strand, and the second oligonucleotide comprises a second polynucleotide continuously complementary to a sequence in the second strand; and
  - ii) at least one component providing a hyperthermophile polymerase activity, thereby generating a nucleic acid amplification product, wherein the nucleic acid amplification product comprises 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases, and the spacer sequence is flanked by the first nucleotide sequence and the second nucleotide sequence; and
- b) detecting the nucleic acid amplification product, wherein detecting the nucleic acid amplification product comprises use of a real-time detection method and is performed in 10 minutes or less from the time the sample nucleic acid is contacted with (a)(i) and (a)(ii), whereby the presence, absence or amount of a target sequence in sample nucleic acid is determined.

D13.1 The kit of embodiment D13, wherein the first oligonucleotide consists essentially of a first polynucleotide continuously complementary to a sequence in the first strand, and the second oligonucleotide consists essentially of a second polynucleotide continuously complementary to a sequence in the second strand; and/or the nucleic acid amplification product consists essentially of 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases.

D13.2 The kit of embodiment D13, wherein the first oligonucleotide consists of a first polynucleotide continuously complementary to a sequence in the first strand, and the second oligonucleotide consists of a second polynucleotide continuously complementary to a sequence in the second strand; and/or the nucleic acid amplification product consists of 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases.

D13.3 The kit of any one of embodiments D1 to D12, further comprising instructions for carrying out a method for determining the presence, absence or amount of a target sequence in sample nucleic acid, the method comprising:
- a) amplifying a target sequence in the sample nucleic acid, wherein:

the target sequence comprises a first strand and a second strand, the first strand and second strand are complementary to each other, and the amplifying comprises contacting non-denatured sample nucleic acid under helicase-free isothermal amplification conditions with:
  - i) a first oligonucleotide and a second oligonucleotide, wherein the first oligonucleotide consists of a first polynucleotide continuously complementary to a sequence in the first strand, and the second oligonucleotide consists of a second polynucleotide continuously complementary to a sequence in the second strand; and
  - ii) at least one component providing a hyperthermophile polymerase activity, thereby generating a nucleic acid amplification product, wherein the nucleic acid amplification product consists of 1) a first nucleotide sequence that is continuously complementary to or substantially identical to the first polynucleotide of the first oligonucleotide, 2) a second nucleotide sequence that is continuously complementary to or substantially identical to the second polynucleotide of the second oligonucleotide, and 3) a spacer sequence comprising 1 to 10 bases, and the spacer sequence is flanked by the first nucleotide sequence and the second nucleotide sequence; and
- b) detecting the nucleic acid amplification product, wherein detecting the nucleic acid amplification product comprises use of a real-time detection method and is performed in 10 minutes or less from the time the sample nucleic acid is contacted with (a)(i) and (a)(ii), whereby the presence, absence or amount of a target sequence in sample nucleic acid is determined.

D14. The kit of any one of embodiments D13 to D13.3, wherein the method does not comprise denaturing the sample nucleic acid prior to or during amplification.

D15. The kit of any one of embodiments D13 to D14, wherein the sample nucleic acid is not contacted with an endonuclease prior to, during, or following amplification.

D16. The kit of any one of embodiments D13 to D15, wherein the sample nucleic acid is unmodified prior to amplification.

D17. The kit of embodiment D16, wherein the unmodified sample nucleic acid is from disrupted cells.

D18. The kit of any one of embodiments D13 to D15, wherein the sample nucleic acid comprises DNA.

D19. The kit of embodiment D18, wherein the sample nucleic acid comprises genomic DNA.

D20. The kit of any one of embodiments D13 to D15, wherein the sample nucleic acid comprises RNA.

D21. The kit of embodiment D20, wherein the sample nucleic acid comprises viral RNA.

D22. The kit of embodiment D20, wherein the sample nucleic acid comprises bacterial RNA.

D23. The kit of any one of embodiments D13 to D22, wherein the sample nucleic acid comprises single-stranded nucleic acid.

D24. The kit of any one of embodiments D13 to D22, wherein the sample nucleic acid comprises double-stranded nucleic acid.

D25. The kit of any one of embodiments D13 to D24, wherein sample nucleic acid is obtained from a subject prior to amplification.

D26. The kit of any one of embodiments D13 to D25, wherein unpurified sample nucleic acid is amplified.

D27. The kit of any one of embodiments D13 to D25, wherein purified sample nucleic acid is amplified.

D28. The kit of any one of embodiments D13 to D27, wherein the method further comprises purifying sample nucleic acid prior to amplification.

D29. The kit of any one of embodiments D13 to D28, wherein the amplification is performed at a constant temperature of about 55 degrees Celsius to about 75 degrees Celsius.

D30. The kit of any one of embodiments D13 to D28, wherein the amplification is performed at a constant temperature of about 55 degrees Celsius to about 65 degrees Celsius.

D31. The kit of any one of embodiments D13 to D28, wherein the amplification is performed at a constant temperature of about 65 degrees Celsius.

D32. The kit of any one of embodiments D13 to D28, wherein the amplification is performed at a constant temperature of about 60 degrees Celsius.

D33. The kit of any one of embodiments D13 to D32, wherein the nucleic acid amplification product is about 20 to 40 bases long.

D34. The kit of any one of embodiments D13 to D33, wherein the spacer sequence comprises 1 to 5 bases.

D35. The kit of any one of embodiments D13 to D34, wherein the spacer sequence is not complementary to or identical to the first polynucleotide of the first oligonucleotide and is not complementary to or identical to the second polynucleotide of the second oligonucleotide.

D36. The kit of any one of embodiments D13 to D35, wherein the spacer sequence is continuously complementary to or substantially identical to a portion of a target sequence in the sample nucleic acid.

D37. The kit of any one of embodiments D13 to D36, wherein detecting the nucleic acid amplification product comprises detection of a fluorescent signal.

D38. The kit embodiment D37, wherein the fluorescent signal is from a molecular beacon.

D39. The kit of any one of embodiments D13 to D38, wherein the method further comprises contacting the nucleic acid amplification product with a signal generating oligonucleotide that comprises i) a polynucleotide complementary to a sequence in the amplification product, and ii) a fluorophore and a quencher.

D40. The kit of any one of embodiments D13 to D39, wherein the method is performed in a single reaction volume.

D41. The kit of any one of embodiments D13 to D40, wherein the method is performed in a single reaction vessel.

D42. The kit of any one of embodiments D13 to D41, wherein the method comprises multiplex amplification.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for detecting a target nucleic acid sequence in a sample, the method comprising:
   (a) contacting a sample RNA in a sample with a reverse transcriptase to generate a cDNA;
   (b) contacting the cDNA with an enzyme having a hyperthermophile polymerase activity to generate a double-stranded DNA (dsDNA), wherein the dsDNA comprises a target nucleic acid sequence, and wherein the target nucleic acid sequence comprises a first strand and a second strand complementary to each other;
   (c) amplifying the target nucleic acid sequence under an isothermal amplification condition, wherein the amplifying comprises contacting the dsDNA with:
      (i) a first primer and a second primer, wherein the first primer is capable of hybridizing to a sequence of the first strand of the target nucleic acid sequence, and the second primer is capable to hybridizing to a sequence of the second strand of the target nucleic acid sequence; and
      (ii) the enzyme having a hyperthermophile polymerase activity, thereby generating a nucleic acid amplification product, wherein the nucleic acid amplification product comprises:
         (1) the sequence of the first primer, and the reverse complement thereof,
         (2) the sequence of the second primer, and the reverse complement thereof, and
         (3) a spacer sequence flanked by (1) the sequence of the first primer and the reverse complement thereof and (2) the sequence of the second primer and the reverse complement thereof, wherein the spacer sequence is 1 to 10 bases long; and
   (d) detecting the nucleic acid amplification product, wherein the detecting is performed in 20 minutes or less from the time the dsDNA is contacted with (c)(i) the first and second primers and (c)(ii) the enzyme having a hyperthermophile polymerase activity, wherein the method does not comprise using any enzymes other than the reverse transcriptase and the enzyme having a hyperthermophile polymerase activity.

2. The method of claim 1, wherein step (c) further comprises determining the amount of the dsDNA that comprises the target nucleic acid sequence in the sample.

3. The method of claim 1, wherein the sample RNA is a cellular RNA, a mRNA, a microRNA, a bacterial RNA, or a viral RNA.

4. The method of claim 1, wherein the target nucleic acid sequence is a bacterial nucleic acid sequence or a viral nucleic acid sequence.

5. The method of claim 1, wherein the enzyme having a hyperthermophile polymerase activity has an amino acid sequence that is at least 90% identical to the amino acid sequence of SEQ ID NO:8 or a functional fragment thereof.

6. The method of claim 1, wherein the enzyme having a hyperthermophile polymerase activity has an amino acid sequence that is at least 95% identical to the amino acid sequence of SEQ ID NO:8.

7. The method of claim 1, wherein the enzyme having a hyperthermophile polymerase activity is a polymerase comprising the amino acid sequence of SEQ ID NO: 8.

8. The method of claim 1, wherein the enzyme having a hyperthermophile polymerase activity has low or no exonuclease activity.

9. The method of claim 1, wherein the sample comprises RNA from prokaryotes or eukaryotes.

10. The method of claim 9, wherein the sample comprises RNA from a virus or a bacterium.

11. The method of claim 1, wherein the method does not comprise contacting the dsDNA with a single-stranded DNA binding protein prior to or during step (c).

12. The method of claim 1, wherein amplifying the target nucleic acid sequence is performed at a constant temperature of about 55 degrees Celsius to about 75 degrees Celsius.

13. The method of claim 12, wherein amplifying the target nucleic acid sequence is performed at a constant temperature of about 65 degrees Celsius.

14. The method of claim 1, wherein the first primer, the second primer, or both is about 8 to 16 bases long.

15. The method of claim 1, wherein the nucleic acid amplification product is about 20 to 40 bases long.

16. The method of claim 1, wherein the spacer sequence comprises a portion of the target nucleic acid sequence.

17. The method of claim 16, wherein the spacer sequence is 1 to 5 bases long.

18. The method of claim 1, further comprising contacting the nucleic acid amplification product with a signal-generating oligonucleotide capable of hybridizing to the amplification product, wherein the single-generating oligonucleotide comprises a fluorophore, a quencher, or both.

19. The method of claim 1, wherein detecting the nucleic acid amplification product comprises detecting a fluorescent signal.

20. The method of claim 19, wherein the fluorescent signal is from a molecular beacon.

21. The method of claim 1, wherein the method is performed in a single reaction vessel.

22. The method of claim 1, wherein the sample RNA is contacted with the reverse transcriptase and the enzyme having a hyperthermophile polymerase activity simultaneously.

23. The method of claim 22, wherein the sample RNA is contacted with the reverse transcriptase, the enzyme having a hyperthermophile polymerase activity, and the first and second primers simultaneously.

24. The method of claim 1, wherein the first primer, the second primer, or both comprises one or more of DNA bases, modified DNA bases, or a combination thereof.

* * * * *

SEQUENCE LISTING

```
<160> NUMBER OF SEQ ID NOS: 12

<210> SEQ ID NO 1
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
ggcttatgga g                                                        11

<210> SEQ ID NO 2
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ataccgctta                                                          10

<210> SEQ ID NO 3
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
gcttatggag                                                          10

<210> SEQ ID NO 4
<211> LENGTH: 28
<212> TYPE: DNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 4
ctggctaccg cttaactcca taagccag                                         28

<210> SEQ ID NO 5
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
aggcttatgg                                                             10

<210> SEQ ID NO 6
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ttataccgct                                                             10

<210> SEQ ID NO 7
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (26)..(29)
<223> OTHER INFORMATION: /note="Phosphorothioate linkage"

<400> SEQUENCE: 7
ccgcgagcct tataccgctt aactcgcgg                                        29

<210> SEQ ID NO 8
<211> LENGTH: 775
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetically derived Thermococcus sp. strain 9 degrees N-7
      polypeptide"

<400> SEQUENCE: 8

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60
```

Val Lys Arg Ala Glu Lys Val Gln Lys Lys Phe Leu Gly Arg Pro Ile
 65                  70                  75                  80

Glu Val Trp Lys Leu Tyr Phe Asn His Pro Gln Asp Val Pro Ala Ile
                 85                  90                  95

Arg Asp Arg Ile Arg Ala His Pro Ala Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Asp Ile Glu Thr
        130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

```
Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Gly Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
                755                 760                 765

Leu Lys Val Lys Gly Lys Lys
                770                 775

<210> SEQ ID NO 9
<211> LENGTH: 775
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetically derived Thermococcus sp. strain 9 degrees N-7
      polypeptide"

<400> SEQUENCE: 9

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45
```

```
Glu Asp Val Lys Lys Val Thr Ala Lys Arg His Gly Thr Val Val Lys
 50                  55                  60
Val Lys Arg Ala Glu Lys Val Gln Lys Lys Phe Leu Gly Arg Pro Ile
 65                  70                  75                  80
Glu Val Trp Lys Leu Tyr Phe Asn His Pro Gln Asp Val Pro Ala Ile
                 85                  90                  95
Arg Asp Arg Ile Arg Ala His Pro Ala Val Val Asp Ile Tyr Glu Tyr
                100                 105                 110
Asp Ile Pro Phe Ala Lys Arg Tyr Leu Ile Asp Lys Gly Leu Ile Pro
                115                 120                 125
Met Glu Gly Asp Glu Glu Leu Thr Met Leu Ala Phe Asp Ile Asp Thr
130                 135                 140
Leu Tyr His Glu Gly Glu Phe Gly Thr Gly Pro Ile Leu Met Ile
145                 150                 155                 160
Ser Tyr Ala Asp Gly Ser Glu Ala Arg Val Ile Thr Trp Lys Lys Ile
                165                 170                 175
Asp Leu Pro Tyr Val Asp Val Ser Thr Glu Lys Glu Met Ile Lys
                180                 185                 190
Arg Phe Leu Arg Val Val Arg Glu Lys Asp Pro Asp Val Leu Ile Thr
                195                 200                 205
Tyr Asn Gly Asp Asn Phe Asp Phe Ala Tyr Leu Lys Lys Arg Cys Glu
                210                 215                 220
Glu Leu Gly Ile Lys Phe Thr Leu Gly Arg Asp Gly Ser Glu Pro Lys
225                 230                 235                 240
Ile Gln Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Lys Pro Lys Glu
                275                 280                 285
Lys Val Tyr Ala Glu Glu Ile Ala Gln Ala Trp Glu Ser Gly Glu Gly
                290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Lys Arg Asn Glu Leu Ala
                355                 360                 365
Pro Asn Lys Pro Asp Glu Arg Glu Leu Ala Arg Arg Gly Gly Tyr
                370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
                435                 440                 445
Ile Pro Ser Leu Leu Gly Asp Leu Leu Glu Glu Arg Gln Lys Ile Lys
450                 455                 460
Arg Lys Met Lys Ala Thr Val Asp Pro Leu Glu Lys Lys Leu Leu Asp
```

```
            465                 470                 475                 480
    Tyr Arg Gln Arg Ala Ile Lys Ile Leu Ala Asn Ser Phe Tyr Gly Tyr
                    485                 490                 495
    Tyr Gly Tyr Ala Lys Ala Arg Trp Tyr Cys Lys Glu Cys Ala Glu Ser
                    500                 505                 510
    Val Thr Ala Trp Gly Arg Glu Tyr Ile Glu Met Val Ile Arg Glu Leu
                    515                 520                 525
    Glu Glu Lys Phe Gly Phe Lys Val Leu Tyr Ala Asp Thr Asp Gly Leu
            530                 535                 540
    His Ala Thr Ile Pro Gly Ala Asp Ala Glu Thr Val Lys Lys Lys Ala
545                 550                 555                 560
    Lys Glu Phe Leu Lys Tyr Ile Asn Pro Lys Leu Pro Gly Leu Leu Glu
                    565                 570                 575
    Leu Glu Tyr Glu Gly Phe Tyr Val Arg Gly Phe Phe Val Thr Lys Lys
                    580                 585                 590
    Lys Tyr Ala Val Ile Asp Glu Glu Gly Lys Ile Thr Thr Arg Gly Leu
                    595                 600                 605
    Glu Ile Val Arg Arg Asp Trp Ser Glu Ile Ala Lys Glu Thr Gln Ala
            610                 615                 620
    Arg Val Leu Glu Ala Ile Leu Lys His Gly Asp Val Glu Glu Ala Val
625                 630                 635                 640
    Arg Ile Val Lys Glu Val Thr Glu Lys Leu Ser Lys Tyr Glu Val Pro
                    645                 650                 655
    Pro Glu Lys Leu Val Ile His Glu Gln Ile Thr Arg Asp Leu Arg Asp
                    660                 665                 670
    Tyr Lys Ala Thr Gly Pro His Val Ala Val Ala Lys Arg Leu Ala Ala
                    675                 680                 685
    Arg Gly Val Lys Ile Arg Pro Gly Thr Val Ile Ser Tyr Ile Val Leu
            690                 695                 700
    Lys Gly Ser Gly Arg Ile Gly Asp Arg Ala Ile Pro Ala Asp Glu Phe
705                 710                 715                 720
    Asp Pro Thr Lys His Arg Tyr Asp Ala Glu Tyr Tyr Ile Glu Asn Gln
                    725                 730                 735
    Val Leu Pro Ala Val Glu Arg Ile Leu Lys Ala Phe Gly Tyr Arg Lys
                    740                 745                 750
    Glu Asp Leu Arg Tyr Gln Lys Thr Lys Gln Val Gly Leu Gly Ala Trp
            755                 760                 765
    Leu Lys Val Lys Gly Lys Lys
            770                 775

<210> SEQ ID NO 10
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
atgcatgcat gc                                                        12

<210> SEQ ID NO 11
<211> LENGTH: 12
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 11
gcatgcatgc at                                                            12

<210> SEQ ID NO 12
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
atgcataaaa aagcatgc                                                      18
```